ns011731924B2

United States Patent
Wang et al.

(10) Patent No.: US 11,731,924 B2
(45) Date of Patent: Aug. 22, 2023

(54) METHODS FOR OPERATING ACETYLENE HYDROGENATION UNITS DURING INTEGRATION OF CHEMICAL PROCESSING SYSTEMS FOR PRODUCING OLEFINS

(71) Applicant: Dow Global Technologies LLC, Midland, MI (US)

(72) Inventors: Hangyao Wang, Pearland, TX (US); Lin Luo, Sugar Land, TX (US); Yu Liu, Lake Jackson, TX (US); Matthew T. Pretz, Lake Jackson, TX (US); Andrzej Malek, Midland, MI (US)

(73) Assignee: Dow Global Technologies LLC, Midland, MI (US)

(*) Notice: Subject to any disclaimer, the term of this patent is extended or adjusted under 35 U.S.C. 154(b) by 0 days.

(21) Appl. No.: 17/621,945

(22) PCT Filed: Jun. 8, 2020

(86) PCT No.: PCT/US2020/036590
§ 371 (c)(1),
(2) Date: Dec. 22, 2021

(87) PCT Pub. No.: WO2020/263546
PCT Pub. Date: Dec. 30, 2020

(65) Prior Publication Data
US 2022/0251005 A1    Aug. 11, 2022

Related U.S. Application Data

(60) Provisional application No. 62/865,583, filed on Jun. 24, 2019.

(51) Int. Cl.
*C07C 7/167* (2006.01)
*B01D 45/16* (2006.01)
(Continued)

(52) U.S. Cl.
CPC .............. *C07C 7/167* (2013.01); *B01D 3/14* (2013.01); *B01D 45/16* (2013.01); *B01J 23/62* (2013.01);
(Continued)

(58) Field of Classification Search
None
See application file for complete search history.

(56) References Cited

U.S. PATENT DOCUMENTS 5,220,097 A * 6/1993 Lam ......................... C10G 5/04
585/259
5,753,583 A * 5/1998 Heineke ............... B01J 37/0232
585/326
(Continued)

FOREIGN PATENT DOCUMENTS

CN      109689600 A     4/2019
WO      2018/024650 A1  2/2018

OTHER PUBLICATIONS

International Search Report and Written Opinion issued by the European Patent Office acting as International Searching Authority for International Patent Application No. PCT/US2020/036590 dated Sep. 25, 2020 (17 total pages).
(Continued)

*Primary Examiner* — Tam M Nguyen
(74) *Attorney, Agent, or Firm* — Dinsmore & Shohl LLP

(57) ABSTRACT

A method for operating an acetylene hydrogenation unit of a steam cracking system that integrates a fluidized catalytic dehydrogenation (FCDh) effluent from a fluidized catalytic dehydrogenation (FCDh) system may include separating a cracked gas from the steam cracking system into at least a hydrogenation feed comprising at least acetylene, CO, and hydrogen, introducing the FCDh effluent to the separation system, combining the FCDh effluent with the cracked gas upstream of the separation system, or both. The method may
(Continued)

include hydrogenating acetylene in the hydrogenation feed. Elevated CO concentration in the hydrogenation feed due to the FCDh effluent may reduce a reaction rate of acetylene hydrogenation. The acetylene hydrogenation unit may operate at an elevated temperature relative to normal operating temperatures when the portion of the FCDh effluent is not integrated, such that a concentration of acetylene in the hydrogenated effluent is less than a threshold acetylene concentration.

15 Claims, 6 Drawing Sheets

(51) Int. Cl.
  *C07C 4/04* (2006.01)
  *B01D 3/14* (2006.01)
  *B01J 23/62* (2006.01)
  *C07C 5/333* (2006.01)
  *C07C 7/00* (2006.01)
  *C07C 7/04* (2006.01)

(52) U.S. Cl.
  CPC .............. *C07C 4/04* (2013.01); *C07C 5/3337* (2013.01); *C07C 7/005* (2013.01); *C07C 7/04* (2013.01); *C07C 2523/62* (2013.01)

(56) References Cited

U.S. PATENT DOCUMENTS

| | | | |
|---|---|---|---|
| 5,847,250 A | 12/1998 | Flick et al. | |
| 5,925,799 A | 7/1999 | Stanley et al. | |
| 8,563,793 B2 | 10/2013 | Zimmermann et al. | |
| 11,584,700 B2* | 2/2023 | Wang | C07C 5/09 |
| 2004/0176652 A1 | 9/2004 | Molinier et al. | |
| 2004/0192982 A1 | 9/2004 | Kuechler et al. | |
| 2006/0025641 A1 | 2/2006 | Gartside et al. | |
| 2006/0173224 A1 | 8/2006 | Putman et al. | |
| 2012/0107182 A1* | 5/2012 | Wegerer | C01B 3/16 |
| | | | 422/111 |
| 2012/0108865 A1* | 5/2012 | Wegerer | C01B 3/16 |
| | | | 585/254 |
| 2014/0249339 A1 | 9/2014 | Simanzhenkov et al. | |
| 2016/0355449 A1 | 12/2016 | Odi et al. | |
| 2016/0362616 A1 | 12/2016 | Oprins | |
| 2017/0137346 A1 | 5/2017 | Bergmeister et al. | |
| 2019/0161422 A1 | 5/2019 | Pretz et al. | |
| 2021/0371357 A1 | 12/2021 | Luo et al. | |
| 2022/0227687 A1* | 7/2022 | Luo | C07C 4/04 |
| 2022/0251006 A1* | 8/2022 | Luo | C07C 7/04 |

OTHER PUBLICATIONS

International Search Report/Written Opinion for PCT/US2020/036586 dated Aug. 28, 2020, pp. 1-17.

International Search Report/Written Opinion for PCT/US2020/036582 dated Sep. 25, 2020, pp. 1-16.

Communication Pursuant to Rules 161/162 for Application No. 20735721.1 dated Feb. 3, 2022—pp. 1-3.

Communication Pursuant to Rules 161/162 for Application No. 20750466.3 dated Feb. 3, 2022—pp. 1-3.

Communication Pursuant to Rules 161/162 for Application No. 20750465.5 dated Feb. 11, 2022—pp. 1-3.

International Preliminary Report on Patentability for Application No. PCT/US2020/036590 dated Dec. 28, 2021, pp. 1-11.

International Preliminary Report on Patentability for Application No. PCT/US2020/036586 dated Dec. 28, 2021, pp. 1-11.

International Preliminary Report on Patentability for Application No. PCT/US2020/03682 dated Dec. 28, 2021, pp. 1-10.

Edgar L. Mohundro, "Overview on C2 and C3 Selective Hydrogenation in Ethylene Plants", 15th Ethylene Produces Conference, 2003 AICHE Spring National Meeting, New Orleans, LA.

Notice of Allowance dated Mar. 29, 2023, pertaining to U.S. Appl. No. 17/621,949, 18 pgs.

Chinese Office Action dated Mar. 4, 2023, pertaining to CN Patent Application No. 202080046062.X, 22 pgs.

Hao et al. "Alleviate CO Effect on Front-end Acetylene Converter", Chemical Industry and Engineering Progress, vol. 21, No. 9, 2002, pp. 673-675.

\* cited by examiner

METHODS FOR OPERATING ACETYLENE HYDROGENATION UNITS DURING INTEGRATION OF CHEMICAL PROCESSING SYSTEMS FOR PRODUCING OLEFINS

CROSS-REFERENCE TO RELATED APPLICATIONS

This application is a National Stage Entry under 35 U.S.C. § 371 of International Patent Application No. PCT/US2020/036590, filed Jun. 8, 2020, which claims priority to U.S. Provisional Patent Application No. 62/865,583, filed on Jun. 24, 2019, the entire disclosures of both of which are hereby incorporated by reference.

BACKGROUND

Field

The present disclosure generally relates to chemical processing systems for producing olefins and the operation thereof and, more specifically, to methods for operating acetylene hydrogenation units in integrated olefin production processes.

Technical Background

Light olefins may be utilized as base materials to produce many types of goods and materials. For example, ethylene may be utilized to manufacture polyethylene, ethylene chloride, or ethylene oxides. Such products may be utilized in product packaging, construction, textiles, etc. Thus, there is an industry demand for light olefins, such as ethylene, propylene, and butene.

Light olefins may be produced by different reaction processes depending on the given chemical feed stream, such as natural gas condensate or a product stream from a petrochemical operation. For example, hydrocarbon cracking (e.g., steam cracking), catalytic dehydrogenation, methanol-to-olefin processes, dehydration processes, or other processes may be used to produce olefins from a hydrocarbon stream. However, hydrocarbon cracking and other processes for producing light olefins can produce byproducts and impurities, such as acetylenic and allenic compounds, which can be poisons to downstream processes and catalysts. Additionally, the presence of high concentrations of acetylene may present a safety concern in downstream processes due to the reactivity of these compounds. Acetylene and other impurities and byproducts can be removed from an olefin-containing hydrocarbon cracking effluent through hydrogenation in a selective hydrogenation process downstream of the hydrocarbon cracking unit. Selective hydrogenation of acetylene compounds in the hydrocarbon cracking effluent can also recover additional product olefins, such as ethylene and propylene.

SUMMARY

In some olefin production processes, light olefins, such as ethylene and propylene for example, may be produced through a combination of one or more olefin production processes, such as steam cracking, fluidized catalytic dehydrogenation (FCDh), methanol-to-oil processes, hydration processes, or other olefin production processes. Because of similarities in the compositions of effluents from these processes, two or more of these separate olefin production processes can be integrated to make use of a single effluent processing system operable to purify and separate the effluent streams. For example, a steam cracking system and an FCDh system can be integrated so that the cracked gas from steam cracking system and at least a portion of the FCDh effluent from the FCDh system can be combined and processed in a common effluent processing system downstream of the steam cracking system and FCDh system. The effluent processing system may include separation and purification systems to isolate product streams and remove unwanted contaminants and reaction byproducts from these product streams. The effluent processing system may include an acetylene hydrogenation unit that may be operable to hydrogenate acetylene produced in at least the steam cracking unit.

Operation of the acetylene hydrogenation unit can be sensitive to the concentration of carbon monoxide (CO) in the feed to the acetylene hydrogenation unit. Not intending to be bound by any particular theory, it is believed that CO interacts with the hydrogenation catalyst in the acetylene hydrogenation unit to decrease the activity of the hydrogenation catalyst for hydrogenating acetylene. Increasing the CO concentration in the feed to the acetylene hydrogenation unit may reduce the conversion of acetylene in the acetylene hydrogenation unit, which can result in breakthrough of acetylene to downstream processes. Breakthrough of acetylene may result in product streams failing to meet purity specification from olefin users, and the greater concentration of acetylene may cause fouling of catalysts in these downstream processes, reducing the efficiency of these processes.

In some cases, a CO concentration in a second process effluent from a second olefin production process may be greater than a CO concentration in a first process effluent from a first olefin production process. For example, an FCDh effluent from an FCDh process may generally have a greater concentration of CO than a concentration of CO in a cracked gas produced by a steam cracking system. Introducing a portion of the second process effluent, such as the FCDh effluent, into the shared effluent processing system may, therefore, significantly increase the concentration of CO in the feed to the acetylene hydrogenation unit as well as the total gas flow rate of the feed to the acetylene hydrogenation unit. The sudden increase in the concentration of CO may result in a fast drop in conversion of acetylene, which may cause increased concentrations of acetylene in the hydrogenated effluent after introducing the second process effluent. The increase in CO concentration in the hydrogenation feed may be compensated for by increasing the temperature of the hydrogenation feed after introducing the portion of the second process effluent. However, for a period of time after introducing the portion of the second process effluent, there remains a high probability of increased acetylene concentrations in the hydrogenated effluent, which can lead to out of specification product streams.

The methods disclosed herein for operating the acetylene hydrogenation unit may reduce the probability of breakthrough of acetylene and out-of-specification product streams when integrating a second process effluent having a greater CO concentration, such as an FCDh effluent, with the first process effluent, such as the cracked gas, in the effluent processing system. In particular, the methods disclosed herein include increasing the conversion of acetylene in a first hydrogenation reactor of the acetylene hydrogenation unit above a threshold acetylene conversion prior to introducing the second process effluent to the effluent processing system. The threshold acetylene conversion may be sufficiently greater than the conversion of acetylene under normal operating conditions so that, when the second process effluent is introduced to the effluent processing system, the decrease in acetylene conversion caused by the increase in the CO contributed by the second process effluent does not result in a concentration of acetylene in the hydrogenated effluent greater than a threshold acetylene concentration. The methods of operating the acetylene hydrogenation unit disclosed herein may reduce or prevent breakthrough of acetylene and out-of-specification product streams when integrating the second process effluent with the cracked gas in the shared effluent processing system.

According to one embodiment presently described, a method for operating an acetylene hydrogenation unit of an integrated system for producing olefins may include separating a first process effluent from a first olefin production process into at least a hydrogenation feed and an acetylene-depleted stream in a separation system. The hydrogenation feed may include at least acetylene, carbon monoxide, and hydrogen. The method may include one or both of introducing at least a portion of a second process effluent from a second olefin production process to the separation system or combining the at least a portion of the second process effluent with the first process effluent upstream of the separation system. Introducing the portion of the second process effluent to the separation system, combining the portion of the second process effluent with the first process effluent, or both, may increase a concentration of carbon monoxide in the hydrogenation feed. The method may further include contacting the hydrogenation feed with an acetylene hydrogenation catalyst in the acetylene hydrogenation unit, the contacting causing hydrogenation of at least a portion of the acetylene in the hydrogenation feed to produce a hydrogenated effluent. An elevated concentration of carbon monoxide in the hydrogenation feed may reduce a reaction rate, independent of temperature, of the hydrogenation of the acetylene. The elevated concentration of carbon monoxide in the hydrogenation feed may be due to the portion of the second process effluent, and the acetylene hydrogenation unit may operate at an elevated temperature relative to normal operating temperatures when the portion of the second effluent is not introduced to the separation system, combined with the first process effluent, or both, such that a concentration of acetylene in the hydrogenated effluent is less than a threshold acetylene concentration.

In some embodiments, the concentration of acetylene in the hydrogenated effluent may not increase above the threshold acetylene concentration during introducing the portion of the second process effluent to the separation system, combining the portion of the second process effluent with the first process effluent, or both. In some embodiments, the threshold acetylene concentration may be less than or equal to 2.0 ppmv, or less than or equal to 1.0 ppmv. In some embodiments, the acetylene hydrogenation unit may include at least a first hydrogenation reactor and a second hydrogenation reactor downstream of the first hydrogenation reactor, and the elevated temperature of the acetylene hydrogenation unit may be sufficient to increase an acetylene conversion in the first hydrogenation reactor, immediately prior to integrating the portion of the second process effluent, to greater than a threshold acetylene conversion, the threshold acetylene conversion being a minimum acetylene conversion in the first hydrogenation reactor, before integration of the portion of the second process effluent, above which the acetylene concentration in the hydrogenated effluent is maintained less than or equal to the threshold acetylene concentration after integrating the portion of the second process effluent.

In some embodiments, the separation system may be a front end depropanizer and the threshold acetylene conversion in the first hydrogenation reactor may be greater than or equal to 0.95 for a flow ratio of less than or equal to 1/12, wherein the flow ratio is a mass flow rate of a portion of the hydrogenation feed contributed by the second process effluent divided by a mass flow rate of another portion of the hydrogenation feed contributed by the first process effluent. In some embodiments, the separation system is a front end depropanizer; a flow ratio is from 1/12 to 1/2, the flow ratio being a mass flow rate of a portion of the hydrogenation feed contributed by the second process effluent divided by a mass flow rate of another portion of the hydrogenation feed contributed by the first process effluent; and the threshold acetylene conversion in the first hydrogenation reactor is greater than or equal a value calculated from $\min[(-0.00024*C_{CO}+0.5*R+0.942), 0.99]$, where $C_{CO}$ is a carbon monoxide concentration in the hydrogenation feed contributed by the cracked gas in parts per million by volume of the hydrogenation feed and R is the flow ratio.

In some embodiments, the separation system may be a front end de-ethanizer and the threshold acetylene conversion in the first hydrogenation reactor may be greater than or equal to 0.99 for a flow ratio less than or equal to 1/2, wherein the flow ratio is a mass flow rate of a portion of the hydrogenation feed contributed by the second process effluent divided by a mass flow rate of another portion of the hydrogenation feed contributed by the first process effluent.

In some embodiments, the method may further include introducing a first portion of the second process effluent to the separation system, combining the first portion of the second process effluent with the first process effluent upstream of the separation system, or both. Introducing the first portion of the second process effluent to the separation system, combining the first portion of the second process effluent with the first process effluent, or both, may increase the concentration of carbon monoxide in the hydrogenation feed and may reduce the conversion of acetylene in the acetylene hydrogenation unit. The method may further include recycling a remaining portion of the second process effluent back to the second olefin production process, increasing a temperature of the acetylene hydrogenation unit to increase the conversion of acetylene in the acetylene hydrogenation unit, and passing at least a second portion of the second process effluent to the separation system, combining at least a second portion of the second process effluent with the first process effluent and the first portion of the second process effluent upstream of the separation system, or both. Integrating the at least a second portion of the second process effluent may further increase the concentration of carbon monoxide in the hydrogenation feed and may reduce the conversion of acetylene in the acetylene hydrogenation unit. In some embodiments, a mass flow rate of a portion of the hydrocarbon feed contributed by the first portion of the second process effluent may be greater than 0% and less than or equal to 12% of the mass flow rate of another portion of the hydrogenation feed contributed by the first process effluent.

In some embodiments, the method may further include increasing a carbon monoxide concentration of the first process effluent prior to introducing the at least a portion of the second process effluent. In some embodiments, the method may further include, after introducing the portion of the second process effluent, decreasing a concentration of carbon monoxide in the first process effluent.

In some embodiments, the acetylene hydrogenation unit may comprise at least a third hydrogenation reactor downstream of the second hydrogenation reactor. In some embodiments, the hydrogenation feed may include at least one product, the at least one product comprising one or more of ethylene, propylene, methane, ethane, propane, or combinations of these. In some embodiments, the first process effluent is a cracked gas from a steam cracking system, and the second process effluent is a fluidized catalytic cracking effluent from a fluidized catalytic cracking (FCDh) system.

According to another aspect of the present disclosure, a method for operating an acetylene hydrogenation unit of a steam cracking system that integrates a fluidized catalytic dehydrogenation (FCDh) effluent from a fluidized catalytic dehydrogenation (FCDh) system may include cracking at least a portion of a first hydrocarbon feed in a steam cracking unit to produce a cracked gas and separating the cracked gas into at least a hydrogenation feed and acetylene-depleted stream in a separation system. The hydrogenation feed may include at least acetylene, carbon monoxide, hydrogen, and at least one product. The method may further include contacting the hydrogenation feed with an acetylene hydrogenation catalyst in the acetylene hydrogenation unit comprising at least a first hydrogenation reactor and a second hydrogenation reactor, the contacting causing hydrogenation of at least a portion of the acetylene in the hydrogenation feed to produce a hydrogenated effluent. The method may further include increasing a temperature of the hydrogenation feed such that a conversion of acetylene in the first hydrogenation reactor is greater than or equal to a threshold acetylene conversion, the threshold acetylene conversion being a minimum acetylene conversion in the first hydrogenation reactor, before integration of the portion of the FCDh effluent, above which the acetylene concentration in the hydrogenated effluent is maintained less than or equal to the threshold acetylene concentration after integrating the portion of the FCDh effluent. The method may further include dehydrogenating at least a portion of a second hydrocarbon feed in the FCDh system to produce the FCDh effluent, the FCDh effluent having a concentration of carbon monoxide greater than a concentration of carbon monoxide in the cracked gas. The method may further include introducing at least a portion of the FCDh effluent to the separation system, combining at least a portion of the FCDh effluent with the cracked gas upstream of the separation system, or both. Introducing the portion of the FCDh effluent to the separation system, combining the portion of the FCDh effluent with the cracked gas, or both, may increase a concentration of carbon monoxide in the hydrogenation feed. An elevated concentration of carbon monoxide in the hydrogenation feed due to the portion of the FCDh effluent may reduces a reaction rate, independent of temperature, of the hydrogenation of the acetylene, the elevated temperature of the acetylene hydrogenation unit relative to normal operating temperatures when the portion of the FCDh effluent is not introduced to the separation system, combined with the cracked gas, or both, may maintain the concentration of acetylene in the hydrogenated effluent less than or equal to a threshold acetylene concentration.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
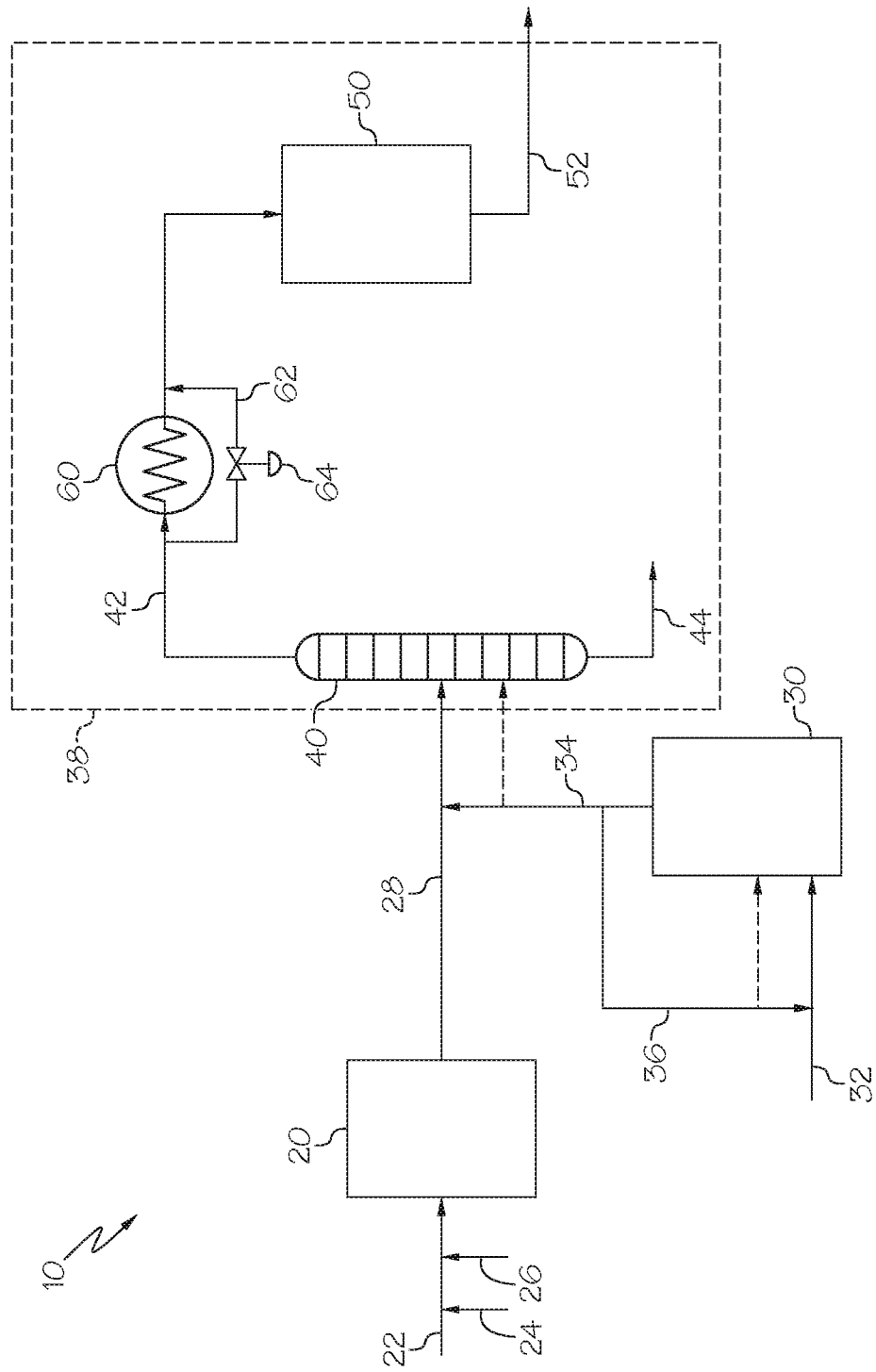
FIG. 1 schematically depicts an integrated process for producing olefins that includes an FCDh system integrated with a steam cracking system and a shared effluent processing system, according to one or more embodiments shown and described herein.

It should be understood that the drawings are schematic in nature, and may not include some components of reactor systems commonly employed in the art, such as, without limitation, sensors, temperature transmitters, pressure transmitters, flow meters, pumps, valves, heat exchangers, internal reactor structures, and the like. It would be known that these components are within the spirit and scope of the present embodiments disclosed. However, operational components, such as those described in the present disclosure, may be added to the embodiments described in this disclosure.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

One or more embodiments of the present disclosure are directed to methods for operating an acetylene hydrogenation unit in an integrated process for producing olefins. In particular, one or more embodiments of the present disclosure are directed to methods for operating an acetylene hydrogenation unit of a steam cracking system that integrates a fluidized catalytic dehydrogenation (FCDh) effluent from a fluidized catalytic dehydrogenation (FCDh) system. The methods may include cracking at least a portion of a first hydrocarbon feed in a steam cracking unit to produce a cracked gas and separating the cracked gas into at least a hydrogenation feed and an acetylene-depleted stream in a separation system. The hydrogenation feed may include at least acetylene, carbon monoxide (CO), and hydrogen. The hydrogenation feed may also include at least one product. The methods may further include contacting the hydrogenation feed with an acetylene hydrogenation catalyst in the acetylene hydrogenation unit that includes a first hydrogenation reactor and a second hydrogenation reactor, the contacting causing hydrogenation of at least a portion of the acetylene in the hydrogenation feed to produce a hydrogenated effluent. The methods may further include increasing the temperature of the hydrogenation feed such that the conversion of acetylene in the first hydrogenation reactor is greater than or equal to a threshold acetylene conversion, the threshold acetylene conversion being a minimum acetylene conversion in the first hydrogenation reactor, before integration of the portion of the FCDh effluent, above which the acetylene concentration in the hydrogenated effluent is maintained less than or equal to the threshold acetylene concentration after integrating the portion of the FCDh effluent.

The methods may include dehydrogenating at least a portion of a second hydrocarbon feed in the FCDh system to produce the FCDh effluent, the FCDh effluent having a concentration of CO greater than a concentration of CO in the cracked gas. The methods may further include introducing at least a portion of the FCDh effluent to the separation system, combining at least a portion of the FCDh effluent with the cracked gas upstream of the separation system, or both, wherein introducing the portion of the FCDh effluent to the separation system, combining the portion of the FCDh effluent with the cracked gas, or both, increases a concentration of CO in the hydrogenation feed. The elevated concentration of CO in the hydrogenation feed due to the portion of the FCDh effluent may reduce a reaction rate, independent of temperature, of the hydrogenation of the acetylene. The elevated temperature of the acetylene hydrogenation unit relative to normal operating temperatures when the portion of the FCDh effluent is not introduced to the separation system, combined with the cracked gas, or both, maintains the concentration of acetylene in the hydrogenated effluent less than or equal to a threshold acetylene concentration. The methods of the present disclosure may enable the FCDh effluent to be integrated with the cracked gas for processing in the separation system and acetylene hydrogenation unit without causing the concentration of acetylene in the hydrogenated effluent to increase above that required by the product specification. Thus, the methods disclosed herein may reduce or prevent off-specification olefin products, which can lead to catalyst fouling, process disruptions, and/or out-of-specification product streams for the downstream polymerization processes.

Described herein is an example of an integrated process for producing olefins that includes steam cracking combined with FCDh and utilizing a single shared effluent processing system having an acetylene hydrogenation unit. The integrated process is utilized to provide context for the methods of operating the acetylene hydrogenation unit presently disclosed, which may reduce or prevent breakthrough of acetylene to downstream processes. It should be understood that the schematic diagrams of FIGS. 1-4 are only example systems, and that other systems suitable for producing olefins are contemplated herein, and the concepts described herein may be utilized in such alternate systems. For example, the concepts described herein may be equally applied to other systems with alternate reactor units and regeneration units, such as those that operate under non-fluidized conditions or are downers rather than risers. Additionally, the presently described methods and processes for processing a chemical stream in a reactor system should not be limited only to embodiments for reactor systems designed to produce light olefins or alkyl aromatics through steam cracking integrated with fluidized catalytic dehydrogenation, such as the reactor system described with respect to FIG. 1, as other processes for producing olefins (e.g., utilizing different feedstocks) are contemplated. Other processes for producing olefins, such as but not limited to methanol-to-olefin processes and hydration processes, may also be included in the integrated system in place or in addition to one or both of the steam cracking unit or the FCDh system.

The reactor systems and methods for processing the chemical streams will now be discussed in further detail with reference to FIG. 1. The chemical stream that is processed may be referred to as a feed stream or simply a feed, which is processed by a reaction, separation, or other process to form a product stream, reactor effluent, or just effluent. The feed may comprise a composition, and depending upon the feed composition, an appropriate catalyst may be utilized to convert the contents of the feed into an effluent that may include light olefins or other chemical products.

As used herein, the term "hydrogenation feed" refers to an effluent from the separation system passed to the acetylene hydrogenation unit that includes at least 95% by mass of the acetylene from the cracked gas introduced to the separation system.

As used herein, the term "acetylene-depleted stream" refers to another effluent stream from the separation system that is different than the hydrogenation feed and includes less than 5% by mass of the acetylene from the cracked gas passed to the separation system.

As used herein, the terms "upstream" and "downstream" are relative to the direction of flow of materials through the integrated process. For example, a first unit operation is upstream of a second unit operation if one or more material streams flow from the first unit operation to the second unit operation. The first unit operation is downstream of the second unit operation if one or more material streams flow from the second unit operation to the first unit operation.

As used herein, the term "selectivity" may refer to a ratio of the moles of a desired product to moles of all the products in a reactor effluent. For example, ethylene selectivity of the acetylene hydrogenation unit may be a ratio of the moles of additionally produced ethylene in the hydrogenated effluent divided by the total moles of all the products produced during the hydrogenation reaction. For example, if all acetylene is converted to ethylene, the selectivity is 100%. If all acetylene is converted to ethane, the selectivity is 0 (zero). And if not only all acetylene but also some of incoming ethylene is converted to ethane, the selectivity then becomes negative.

As used herein, the term "breakthrough" may refer to passing of a specific reactant, such as but not limited to, acetylene, methyl acetylene, propadiene, or other compound, from one processing unit to another downstream processing unit in an amount greater than a threshold value specified by the olefin users, for example 2 parts per million by volume (ppmv). In an example, breakthrough may occur when the specific reactant undergoes substantially incomplete conversion in a reaction system so that an effluent passed out of the reaction system has a concentration of the specific reactant of greater than 2 part per million by volume (ppmv), or greater than 1 ppmv depending on olefin users and the location.

As used herein, the term "threshold acetylene concentration" may refer to a concentration of acetylene in a hydrogenated effluent from the acetylene hydrogenation unit at or below which the concentration of acetylene is considered to be within the specifications for product purity provided by olefin users and/or does not cause fouling of catalysts or other disruptions in downstream processes.

As used herein, the term "thermal runaway" may refer to a condition of a process in which an incremental increase in temperature of the process changes the operating conditions in a manner that produces or generates heat, which further increases the temperature.

Referring to FIG. 1, an integrated process 10 for producing olefins is schematically depicted. The integrated process 10 may include a steam cracking system 20, a fluidized catalytic cracking (FCDh) system 30, and an effluent processing system 38, which may be operable to process the product effluents from the steam cracking system 20 and the FCDh system 30. The steam cracking system 20 may be operable to convert at least a portion of a first hydrocarbon feed 22 to produce a cracked gas 28 that includes at least hydrogen, carbon monoxide (CO), acetylene, and at least one steam cracker product. The FCDh system 30 may be operable to convert at least a portion of a second hydrocarbon feed 32 to produce an FCDh effluent 34 that includes at least hydrogen, CO, and at least one FCDh product. The cracked gas 28, or the cracked gas 28 and at least a portion of the FCDh effluent 34, may be passed to the effluent processing system 38, which may be operable to process the cracked gas 28 and/or the FCDh effluent 34 to produce one or more product streams (not shown). The effluent processing system 38 may include at least a separation system 40, an acetylene hydrogenation unit 50 downstream of the separation system 40, and a heat exchanger 60 disposed between the separation system 40 and the acetylene hydrogenation unit 50. The effluent processing system 38 may include additional separation and/or purification processes (not shown) disposed downstream of the acetylene hydrogenation unit 50.

Figure 2:
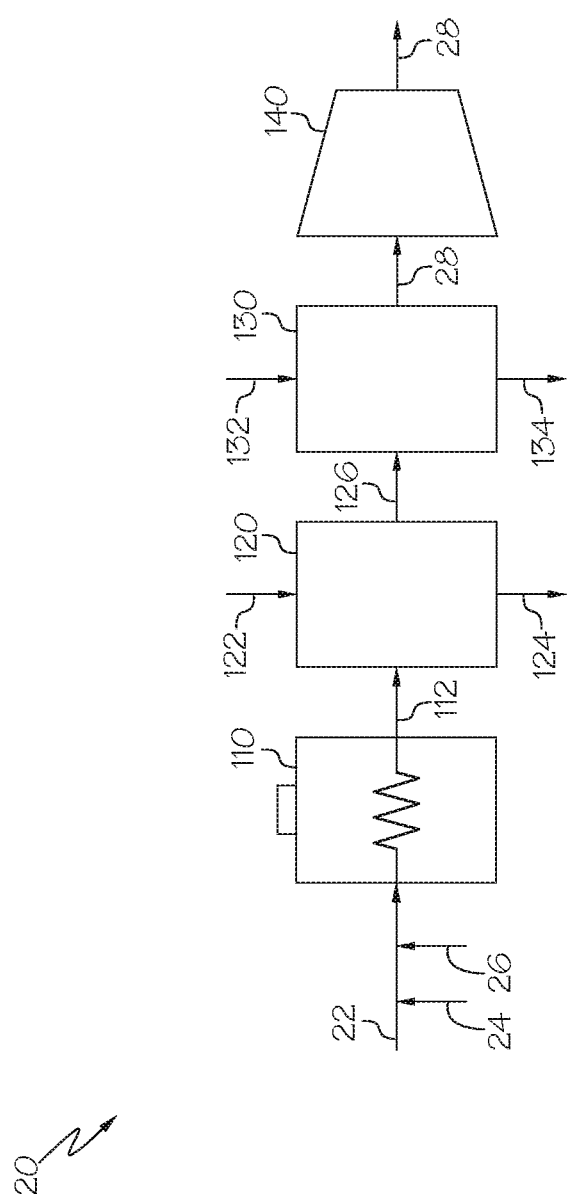
FIG. 2 schematically depicts the steam cracking system of the integrated process of FIG. 1, according to one or more embodiments shown and described herein.

Referring to FIG. 2, an embodiment of a steam cracking system 20 is schematically depicted. The steam cracking system 20 may include a steam cracking unit 110 and one or more of an oil quench unit 120, a water quench unit 130, a compressor system 140, or combinations of these. In some embodiments, the steam cracking system 20 may also include an acid gas removal unit (not shown). The first hydrocarbon feed 22 may be introduced to the steam cracking unit 110 for cracking one or more hydrocarbon constituents of the first hydrocarbon feed 22 to produce one or more olefins. The first hydrocarbon feed 22 may be any hydrocarbon stream, such as a product stream from a petrochemical process or a refining operation for crude oil, shale gas, or other hydrocarbon sources. In some embodiments, the first hydrocarbon feed 22 may include a plurality of different hydrocarbon streams combined prior to or in the steam cracking unit 110. In some embodiments, the first hydrocarbon feed 22 may be a light hydrocarbon feedstock, such as a feedstock including ethane, propane, butane, naphtha, other light hydrocarbon, or combinations of these.

The steam cracking unit 110 may be operable to receive the first hydrocarbon feed 22 and crack one or more constituents of the first hydrocarbon feed 22 to produce a cracker effluent 112. The steam cracking unit 110 may be operable to contact the first hydrocarbon feed 22 with steam at temperatures of from 500° C. to 850° C. to produce the cracker effluent 112. A sulfur-containing composition 24, a methanol-containing stream 26, or both, may also be introduced to the steam cracking unit 110. The sulfur-containing composition 24, the methanol-containing stream 26, or both, may be introduced directly into the steam cracking unit 110 or may be combined with the first hydrocarbon feed 22 upstream of the steam cracking unit 110. The sulfur-containing composition 24 may include one or more sulfur-containing compounds, such as, but not limited to dimethyl disulfide (DMDS), dimethyl sulfide (DMS), diethyl disulfide (DEDS), methyl mercaptan (MM), or combinations thereof. The sulfur-containing compounds from the sulfur-containing composition 24 may passivate the heating coil in the steam cracking furnace of the steam cracking unit 110 to manage the formation of coke in the steam cracking unit 110. Increasing or decreasing the sulfur-containing compounds may change an amount of CO generated in the steam cracking unit 110, thereby changing the CO concentration (e.g., amount of CO) in the cracker effluent 112.

Ethane, propane, naphtha, and other hydrocarbons present in the first hydrocarbon feed 22 may be steam cracked in the steam cracking unit 110 to produce at least one or more light olefins, such as but not limited to ethylene, propylene, butenes, or combinations of these. The steam cracking unit 110 may be operated under conditions (i.e., temperature, pressure, residence time, etc.) sufficient to produce one or more light olefins, such as ethylene and propylene, from the hydrocarbons in the first hydrocarbon feed 22. In some embodiments, the steam cracking unit 110 may be operated at a temperature of from 500° C., to 850° C., from 500° C. to 810° C., from 550° C. to 850° C., from 550° C. to 810° C., from 600° C. to 850° C., or from 600° C. to 810° C. The temperature of the steam cracking unit 110 may depend on the composition of the first hydrocarbon feed 22 introduced to the steam cracking unit 110. Other suitable operating conditions for hydrocarbon cracking processes are well known in the art.

The cracker effluent 112 may include one or more cracking reaction products, such as, but not limited to, ethylene, propylene, butenes (e.g., 1-butene, trans-2-butene, cis-2-butene, isobutene), ethane, propane, other light hydrocarbons, or combinations of these. The cracker effluent 112 can also include hydrogen, CO, acetylene, methyl acetylene, propadiene, methane, other compounds produced in the steam cracking unit 110, unreacted constituents of the first hydrocarbon feed 22, or combinations of these. For example, the cracking reactions in the steam cracking unit 110 may produce byproducts, such as hydrogen and CO, and side-reaction products, such as acetylene, methyl acetylene, propadiene, other side-reaction products, or combinations of these. Additionally, unreacted hydrocarbons and/or other constituents of the first hydrocarbon feed 22 may pass through the steam cracking unit 110 without undergoing reaction so that the cracker effluent 112 includes these unreacted constituents of the first hydrocarbon feed 22. Acid and alcohol gases may also be produced in the steam cracking unit 110.

Referring still to FIG. 2, the cracker effluent 112 may be passed from the steam cracking unit 110 to the oil quench unit 120 downstream of the steam cracking unit 110. The oil quench unit 120 maybe operable to quench the cracker effluent 112 with a hydrocarbon quench liquid 122 to reduce the temperature of the cracker effluent 112 and remove heavy hydrocarbon constituents to produce an oil-quench effluent 126. The oil-quench effluent 126 may be passed from the oil quench unit 120 to the water quench unit 130 downstream of the oil quench unit 120. The water quench unit 130 maybe operable to quench the cracker effluent 112 with liquid water to further reduce the temperature of the oil-quench effluent 126 and remove steam to produce the cracked gas 28. Although the water quench unit 130 is shown in FIG. 2 as being downstream of the oil quench unit 120, it is understood that the water quench unit 130 may alternatively be positioned upstream of the oil quench unit 120. The steam cracking system 20 may optionally include an acid gas removal system (not shown) for removing acid gases from the cracked gas 28. Alternatively, in some embodiments, the acid gas removal system may be incorporated into the effluent processing system 38 (FIG. 1). The cracked gas 28 may be passed to a compression system 140 operable to reduce the volume of the cracked gas 28 upstream of the effluent processing system 38.

Figure 3:
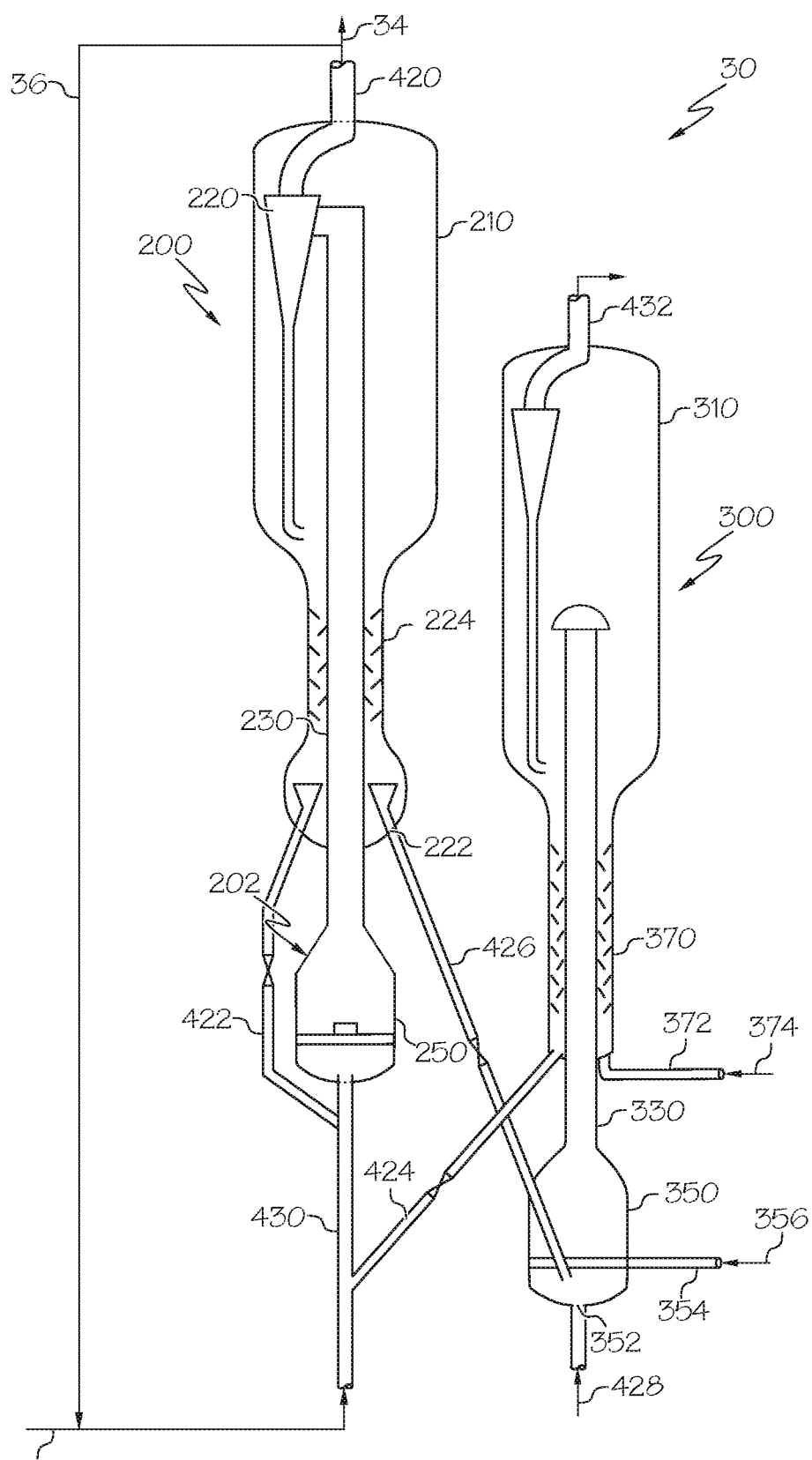
FIG. 3 schematically depicts the FCDh system of the integrated process of FIG. 1, according to one or more embodiments shown and described herein.

Referring now to FIG. 3, the FCDh system 30 may be operable to receive a second hydrocarbon feed 32 and contact the second hydrocarbon feed 32 with a dehydrogenation catalyst to produce an FCDh effluent 34. The second hydrocarbon feed 32 to the FCDh system 30 may include at least one of propane, n-butane, iso-butane, ethane, or ethylbenzene. The second hydrocarbon feed 32 may include one or more hydrocarbon streams from a hydrocarbon processing facility. In some embodiments, the second hydrocarbon feed 32 may include a propane or ethane stream recovered from the effluent processing system 38 and recycled back to the FCDh system 30. In the FCDh system 30, at least a portion of the second hydrocarbon feed 32 may be converted to light olefins or other products through dehydrogenation in the presence of a dehydrogenation catalyst. The dehydrogenation catalyst may be any catalyst known in the art for dehydrogenating hydrocarbons to produce olefins. The FCDh effluent 34 may include at least CO, hydrogen, and at least one FCDh product. The at least one FCDh product may include one or more of ethylene, propylene, or combinations thereof.

Referring to FIG. 3, an example FCDh system 30 is schematically depicted. The FCDh system 30 may include a reactor portion 200 and a catalyst processing portion 300. As used herein in the context of FIG. 1, the reactor portion 200 may refer to a portion of the FCDh system 30 in which the major process reaction takes place. For example, the second hydrocarbon feed 32 may be dehydrogenated in the presence of the dehydrogenation catalyst in the reactor portion 200 of the FCDh system 30. The reactor portion 200 comprises a reactor 202, which may include a downstream reactor section 230, an upstream reactor section 250, and a catalyst separation section 210, which serves to separate the catalyst from the chemical products formed in the reactor 202.

Also, as used herein, the catalyst processing portion 300 of the FCDh system 30 of FIG. 3 generally refers to the portion of the FCDh system 30 in which the catalyst is in some way processed, such as removal of coke deposits, heating of the catalyst, reactivating the catalyst, other processing operations, or combinations of these, during normal operation of the FCDh system 30. In some embodiments, the catalyst processing portion 300 may include a combustor 350, a riser 330, a catalyst separation section 310, and an oxygen treatment zone 370. The combustor 350 of the catalyst processing portion 300 may include one or more lower combustor inlet ports 352 and may be in fluid communication with the riser 330. The combustor 350 may be in fluid communication with the catalyst separation section 210 via transfer line 426, which may supply deactivated catalyst (during normal operating conditions) from the reactor portion 200 to the catalyst processing portion 300 for catalyst processing (e.g., coke removal, heating, reactivating, etc.). The oxygen treatment zone 370 may be in fluid communication with the upstream reactor section 250 (e.g., via transfer line 424 and transport riser 430), which may supply processed catalyst from the catalyst processing portion 300 back to the reactor portion 200. The combustor 350 may include the lower combustor inlet port 352 where air inlet 428 connects to the combustor 350. The air inlet 428 may supply air or other reactive gases, such as an oxygen-containing gas to the combustor 350. Air and/or other reactive gases, may be introduced to the combustor 350 to aid in combustion of a supplemental fuel. The combustor 350 may also include a fuel inlet 354. The fuel inlet 354 may supply a fuel, such as a hydrocarbon stream 356 to the combustor 350. The oxygen treatment zone 370 may include an oxygen-containing gas inlet 372, which may supply an oxygen-containing gas 374 to the oxygen treatment zone 370 for oxygen treatment of the catalyst.

Referring to FIG. 3, general operation of the FCDh system 30 to conduct a continuous reaction under normal operating conditions will be described. During operation of the reactor portion 200 of the FCDh system 30, the second hydrocarbon feed 32 may enter the transport riser 430, and FCDh effluent 34 may exit the FCDh system 30 via pipe 420. According to one or more embodiments, the FCDh system 30 may be operated by feeding the second hydrocarbon feed 32 and a fluidized dehydrogenation catalyst into the upstream reactor section 250. Hydrocarbons in the second hydrocarbon feed 32 may contact the dehydrogenation catalyst in the upstream reactor section 250, and each may flow upwardly into and through the downstream reactor section 230 to produce at least one FCDh product under normal operating conditions.

The FCDh effluent 34 and the dehydrogenation catalyst may be passed out of the downstream reactor section 230 to a separation device 220 in the catalyst separation section 210. The FCDh effluent 34 may include hydrogen, CO, and at least one FCDh product. The FCDh effluent 34 may also include unreacted portions of the second hydrocarbon feed 32, fluidization gases, byproducts, reaction intermediates, other gases, or combinations of these. The at least one FCDh product may include ethylene, propylene, or other light olefins. The FCDh effluent 34 may have a CO concentration greater than the concentration of CO in the cracked gas 28 from the steam cracking system 20. The FCDh effluent 34 may have a concentration of CO of from 600 parts per million by volume (ppmv) to 2400 ppmv, such as from 1000 ppmv to 2000 ppmv.

The dehydrogenation catalyst may be separated from the FCDh effluent 34 in the separation device 220. The FCDh effluent 34 may then be transported out of the catalyst separation section 210. For example, the separated vapors of the FCDh effluent 34 may be removed from the FCDh system 30 via a pipe 420 at a gas outlet port of the catalyst separation section 210. In some embodiments, the separation device 220 may be a cyclonic separation system, which may include two or more stages of cyclonic separation.

According to some embodiments, following separation from vapors of the FCDh effluent 34 in the separation device 220, the dehydrogenation catalyst may generally move through the stripper 224 to the reactor catalyst outlet port 222 where the dehydrogenation catalyst may be transferred out of the reactor portion 200 via transfer line 426 and into the catalyst processing portion 300. Optionally, the dehydrogenation catalyst may also be transferred directly back into the upstream reactor section 250 via standpipe 422. In some embodiments, recycled dehydrogenation catalyst from the stripper 224 may be premixed with processed dehydrogenation catalyst from the catalyst processing portion 300 in the transport riser 430.

The separated dehydrogenation catalyst may be passed from the catalyst separation section 210 to the combustor 350 of the catalyst processing portion 300. The dehydrogenation catalyst may be processed in the catalyst processing portion 300 during normal operation to remove coke deposits, heat the catalyst, reactivate the catalyst, other catalyst processing, or any combinations of these. As previously discussed, processing the dehydrogenation catalyst in the catalyst processing portion 300 may include removing coke deposits from the catalyst, raising the temperature of the catalyst through combustion of a combustion fuel source, reactivating the catalyst, stripping one or more constituents from the catalyst, other processing operation, or combinations of these. In some embodiments, processing the dehydrogenation catalyst in the processing portion 300 may include combusting a combustion fuel source in the presence of the dehydrogenation catalyst in the combustor 350 to remove coke deposits and/or heat the dehydrogenation catalyst to produce a heated catalyst. The heated dehydrogenation catalyst may be separated from the combustion gases in the catalyst separation section 310.

In some embodiments, the heated dehydrogenation catalyst may then be reactivated by conducting an oxygen treatment of the heated dehydrogenation catalyst. The oxygen treatment may include exposing the heated dehydrogenation catalyst to an oxygen-containing gas 374 for a period of time sufficient to reactivate the dehydrogenation catalyst. The oxygen treatment to reactivate the dehydrogenation catalyst may be conducted after combustion of the supplemental fuel to heat the dehydrogenation catalyst. The oxygen treatment may include treating the heated dehydrogenation catalyst with the oxygen-containing gas 374 for a period of at least two minutes, which may reactivate the dehydrogenation catalyst to produce a reactivated dehydrogenation catalyst. The oxygen-containing gas 374 may include an oxygen content of from 5 mole % to 100 mole % based on total molar flow rate of the oxygen-containing gas 374. In some embodiments, the oxygen treatment of the dehydrogenation catalyst may include maintaining the dehydrogenation catalyst at a temperature of at least 660° C. while exposing the dehydrogenation catalyst to a flow of the oxygen-containing gas 374 for a period of time greater than two minutes and sufficient to produce a reactivated dehydrogenation catalyst having a catalytic activity that is greater than the heated dehydrogenation catalyst after being heated by combustion of the supplemental fuel. The oxygen treatment may be conducted in the oxygen treatment zone 370, which may be downstream of the catalyst separation section 310 of the catalyst processing portion 300.

The combustion gases from combustion of coke and/or the supplemental fuel during processing of the dehydrogenation catalyst or other gases introduced to the dehydrogenation catalyst during catalyst processing and catalyst reactivation may be removed from the catalyst processing portion 300 via a regenerator effluent outlet 432.

FIG. 3 and the preceding discussion present one embodiment of a system for catalytically dehydrogenating hydrocarbons to produce light olefins. However, it is understood that other reactor system configurations may be employed for catalytic dehydrogenation of hydrocarbons to produce light olefins without departing from the scope of the present disclosure. For example, in some embodiments, the FCDh system 30 may include any type of fluidized reactor system operable to contact the second hydrocarbon feed 32 with a catalyst in a fluidization regime, such as bubbling regime, slug flow regime, turbulent regime, fast fluidization regime, pneumatic conveying regime, or combinations thereof.

Referring again to FIG. 3, the FCDh system 30 may be operated in system recycle in which at least a portion of the FCDh effluent 34 is recycled back to the reactor portion 200 of the FCDh system 30. The FCDh system 30 may be operated in system recycle mode during start-up of the FCDh system 30 or in response to an off-spec event in which the composition of the FCDh effluent 34 does not conform to the product stream target standards. In these situations, the FCDh effluent 34 may be recycled back to the FCDh system 30 while adjustments are made to the FCDh system 30 to bring the composition of the FCDh effluent 34 back into conformance. System recycle may also occur when the reactor system is integrated with another reactor system (e.g., such as the steam cracking system 20) and the other reactor system experiences an interruption (e.g., planned events such as planned maintenance or unplanned events such unexpected failures of equipment such as furnace, compressors, or other equipment). During system recycle operation, at least a portion of or all of the FCDh effluent 34 may be recycled back to the FCDh system 30 in an FCDh effluent recycle 36. The FCDh effluent recycle 36 may be combined with the second hydrocarbon feed 32 upstream of the transport riser 430 as shown in FIG. 3. In some embodiments, the FCDh effluent recycle 36 may be passed directly to the transport riser 430, in which the FCDh effluent recycle 36 is then combined with the second hydrocarbon feed 32 and the dehydrogenation catalyst.

Figure 4:
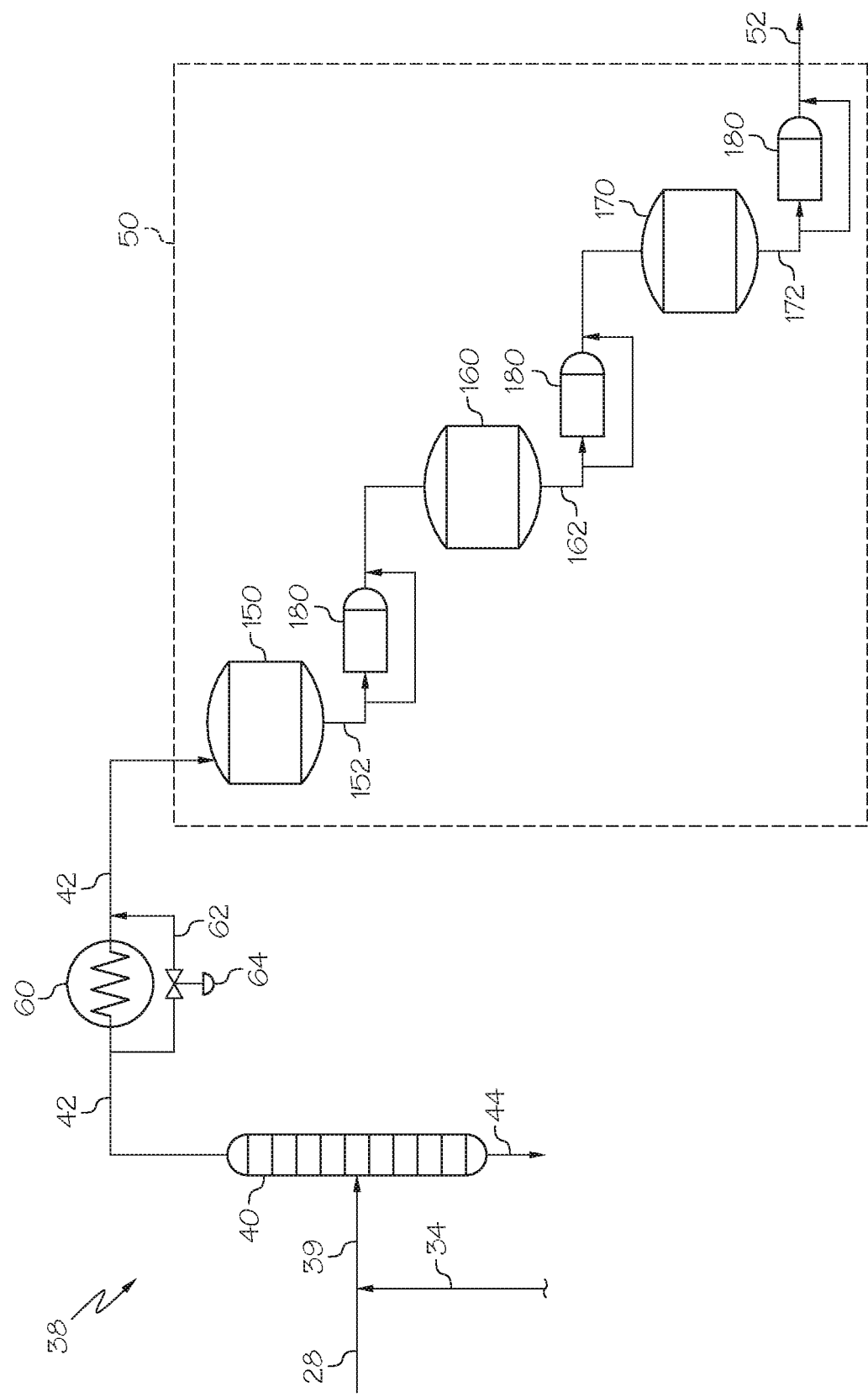
FIG. 4 schematically depicts a portion of the effluent processing system of the integrated process of FIG. 1, according to one or more embodiments shown and described herein.

Referring to FIG. 4, as previously discussed, the effluent processing system 38 may include at least the separation system 40, the acetylene hydrogenation unit 50 downstream of the separation system 40, and the heat exchanger 60 disposed between the separation system 40 and the acetylene hydrogenation unit 50. The cracked gas 28, at least a portion of the FCDh effluent 34, or both may be passed to the separation system 40. In some embodiments, the cracked gas 28 and the FCDh effluent 34 may be independently passed directly to the separation system 40. In some embodiments, the cracked gas 28 and the FCDh effluent 34 may be combined upstream of the separation system 40 and passed as a combined stream 39. The FCDh effluent 34 may be combined with the cracked gas 28 at any point downstream of the water quench unit 130 and oil quench unit 120.

The separation system 40 may be operable to produce at least the hydrogenation feed 42 and an acetylene-depleted stream 44 from the cracked gas 28, the FCDh effluent 34, or both. The separation system 40 may include one or a plurality of separation units. The separation system 40 may include any type of separation units operable to produce the hydrogenation feed 42 from the cracked gas 28, the FCDh effluent 34, or both. In some embodiments, the separation system 40 may include a distillation unit in which the cracked gas 28, the FCDh effluent 34, or both may be separated into the hydrogenation feed 42 and the acetylene-depleted stream 44 by differences in boiling point temperatures of the constituents. In some embodiments, the separation system 40 may be a multiple-stage distillation column. Separation of the constituents of the cracked gas 28, the FCDh effluent 34, or both by difference in boiling point temperature may include initially cooling the cracked gas 28, the FCDh effluent 34, or both to temperatures less than the boiling point temperatures of one or more constituents. Thus, the separation system 40 may include a condenser operable to condense one or more constituents of the cracked gas 28, the FCDh effluent 34, or both upstream of the distillation unit. The separation system 40 is not limited to a distillation process. It is understood that other methods and processes for producing the hydrogenation feed 42 from the cracked gas 28, the FCDh effluent 34, or both are contemplated.

As previously discussed, the hydrogenation feed 42 may include at least 95% by weight of the acetylene from the cracked gas 28 passed to the separation system 40. The hydrogenation feed 42 may include saturated and unsaturated hydrocarbons, such as, but not limited to, ethylene ($C_2H_4$), propylene ($C_3H_6$), acetylene ($C_2H_2$), methyl acetylene ($H_3C-C\equiv CH$), propadiene ($HC=C=CH$), methane ($CH_4$), ethane ($C_2H_6$), propane ($C_3H_8$), or combinations of these. The hydrogenation feed 42 may also include non-hydrocarbon gases, such as, but not limited to, hydrogen, CO, carbon dioxide ($CO_2$), inert gases, or combinations of these. Inert gases may include nitrogen, argon, or other inert gases present in the steam cracking system 20, the FCDh system 30, or both. In some embodiments, the hydrogenation feed 42 may include acetylene, hydrogen, CO, and at least one product. The hydrogenation feed 42 may further include methyl acetylene, propadiene, or both. The product in the hydrogenation feed 42 may include one or more of ethylene, propylene, methane, ethane, propane, or combinations of these.

The acetylene-depleted stream 44 may include less than 5% by weight of the acetylene from the cracked gas 28. The acetylene-depleted stream 44 may include a greater weight percentage of higher boiling point hydrocarbons compared to the hydrogenation feed 42. These higher boiling point hydrocarbons may include saturated and unsaturated hydrocarbons, such as, but not limited to propane, propylene, butane, butenes, butadiene, pentane, or other higher boiling temperature hydrocarbons.

The separation system 40 may be a front end depropanizer (FEDP) or a front end de-ethanizer (FEDE). When the separation system 40 is an FEDP, the hydrogenation feed 42 may include $C_{3-}$ hydrocarbons and non-hydrocarbon gases. The $C_{3-}$ hydrocarbons may include, but are not limited to, methane, ethane, propane, ethylene, propylene, acetylene, methyl acetylene, propadiene, and combinations of these. The light gases in the hydrogenation feed 42 may include hydrogen, CO, carbon dioxide, nitrogen, or other non-hydrocarbon gases. When the separation system 40 is an FEDP, the acetylene-depleted stream 44 may include the $C_{4+}$ hydrocarbons, such as butane, butenes, butadiene, pentane, pentenes (i.e., one or more of the various isomers of pentene), and other $C_{4+}$ hydrocarbons. In some embodiments, the separation system 40 may be an FEDE, in which case, the greater portions of the propane and propylene may be in the acetylene-depleted stream 44 rather than in the hydrogenation feed 42. In some embodiments, when the separation system 40 is an FEDE, the acetylene-depleted stream 44 may include the greater fraction of methyl acetylene and propadiene compared to the hydrogenation feed 42. Further information on various front end configurations for acetylene hydrogenation in olefin production processes can be found in "Overview on C2 and C3 Selective Hydrogenation in Ethylene Plants" by Edgar L. Mohundro, 15th Ethylene Produces Conference, 2003 AICHE Spring National Meeting, New Orleans, La., the entire contents of which are incorporated herein by reference.

Referring to FIG. 4, the effluent processing system 38 may include the acetylene hydrogenation unit 50 downstream of the separation system 40 and positioned to receive the hydrogenation feed 42 from the separation system 40. The hydrogenation feed 42 may be passed from the separation system 40 to the acetylene hydrogenation unit 50. The hydrogenation feed 42 may be contacted with a hydrogenation catalyst in the acetylene hydrogenation unit 50. The contacting of the hydrogenation feed 42 with the hydrogenation catalyst may cause hydrogenation of at least a portion of the acetylene in the hydrogenation feed 42 to produce the hydrogenated effluent 52, which may have a reduced concentration of acetylene compared to the hydrogenation feed 42. The hydrogenated effluent 52 may include reaction products from the hydrogenation reaction and unreacted constituents of the hydrogenation feed 42. The acetylene hydrogenation unit 50 may include one or a plurality of hydrogenation reactors, such as 1, 2, 3, or more than 3 hydrogenation reactors. The hydrogenation reactors of the acetylene hydrogenation unit 50 may be fixed bed reactors comprising a fixed bed of the hydrogenation catalyst with reactants and products in vapor phase.

Referring to FIG. 4, in some embodiments, the acetylene hydrogenation unit 50 may include a plurality of hydrogenation reactors arranged in series (e.g., first hydrogenation reactor 150, second hydrogenation reactor 160, and third hydrogenation reactor 170). Referring to FIG. 4, in one embodiment, the acetylene hydrogenation unit 50 may include at least a first hydrogenation reactor 150 and a second hydrogenation reactor 160 downstream of the first hydrogenation reactor 150. The acetylene hydrogenation unit 50 may also include a third hydrogenation reactor 170 downstream of the second hydrogenation reactor 160. The acetylene hydrogenation unit 50 may also optionally include heat exchangers 180 disposed between each of the hydrogenation reactors. The heat exchangers 180 may be operable to remove heat generated from the exothermic hydrogenation reaction between the hydrogenation reactors.

The hydrogenation feed 42 may be passed to the first hydrogenation reactor 150, which may be operable to hydrogenate at least acetylene from the hydrogenation feed 42 to produce a first hydrogenated effluent 152. The first hydrogenated effluent 152 may have a concentration of acetylene less than the concentration of acetylene in the hydrogenation feed 42. The first hydrogenation reactor 150 may have an acetylene conversion of greater than or equal to 85%, greater than or equal to 90%, or greater than or equal to 95% during normal operating conditions of the acetylene hydrogenation unit 50 in order to maintain the concentration of acetylene in the hydrogenated effluent 52 less than the threshold acetylene concentration. Heat may be removed from the first hydrogenated effluent 152 by passing the first hydrogenated effluent 152 through a heat exchanger 180. The first hydrogenated effluent 152 may be passed on the to the second hydrogenation reactor 160, which may be operable to further hydrogenate acetylene in the first hydrogenated effluent 152 to produce a second hydrogenated effluent 162. Heat may be removed from the second hydrogenated effluent 162 by passing the second hydrogenated effluent 162 through a heat exchanger 180. The second hydrogenated effluent 162 may be passed on the to the third hydrogenation reactor 170, which may be operable to further hydrogenate acetylene in the second hydrogenated effluent 162 to produce a third hydrogenated effluent 172. Heat may be removed from the third hydrogenated effluent 172 by passing the third hydrogenated effluent 172 through a heat exchanger 180. The third hydrogenated effluent 172 may be passed out of the acetylene hydrogenation unit 50 as the hydrogenated effluent 52.

Although not depicted in the figures, the acetylene hydrogenation unit 50 may include one or a plurality of temperature sensors, pressure sensors, flow meters, or combinations of these for measuring the temperature, pressure, or gas flow rates at one or a plurality of positions of the acetylene hydrogenation unit 50. The temperature, pressure, and/or gas flow rate may be determined for one or more of the plurality of acetylene hydrogenation reactors of the acetylene hydrogenation unit 50 and/or for the hydrogenation feed 42 introduced to the acetylene hydrogenation unit 50. The method of operating the acetylene hydrogenation unit 50 may include determining the temperature of the acetylene hydrogenation unit 50, an temperature of the hydrogenation feed 42 passed to the acetylene hydrogenation unit 50, or both.

The acetylene hydrogenation unit 50 may also include one or a plurality of analyzers, such as GC analyzers, operable to measure the concentration of CO, hydrogen, or other constituents in the hydrogenation feed 42, the hydrogenated effluent 52, intermediate effluents from one or more of the hydrogenation reactors of the acetylene hydrogenation unit 50, or combinations of these. In some embodiments, the stream for composition analysis may be retrieved from the hydrogenation feed 42 before introducing the hydrogenation feed 42 to the acetylene hydrogenation unit 50. Alternatively or additionally, the stream for composition analysis may be retrieved from the hydrogenated effluent 52 passed out of the acetylene hydrogenation unit 50. In some embodiments, the stream for composition analysis may be retrieved from one or more intermediate effluent streams passed of one of the hydrogenation reactors of the acetylene hydrogenation unit 50. The method of operating the acetylene hydrogenation unit 50 may include determining the concentration of CO, hydrogen, or other constituent in the acetylene hydrogenation unit 50.

The hydrogenation catalyst may be an acetylene hydrogenation catalyst that is a catalyst selective for hydrogenating acetylene relative to product compounds in the hydrogenation feed 42. The hydrogenation catalyst may be any known catalyst for selectively hydrogenating acetylene. Commercial catalysts for acetylene hydrogenation are widely available, and the present disclosure is not limited to any specific composition recited herein.

The acetylene hydrogenation unit 50 can be operated at conditions under which the catalytic hydrogenation is selective for hydrogenation of acetylene over hydrogenation of propylene and ethylene. The acetylene hydrogenation unit 50 may be operated at a temperature sufficient to hydrogenate acetylene at a conversion rate that prevents breakthrough of acetylene to downstream processes, but less than a temperature resulting in increased hydrogenation of olefins and thermal runaway of the acetylene hydrogenation unit 50. The operating temperature of the acetylene hydrogenation unit 50 may be from 10° C. to 200° C., such as from 10° C. to 100° C., although the operating temperature of the acetylene hydrogenation unit 50 may depend on the composition of the hydrogenation feed 42, as will be discussed in further detail herein. Other factors influencing the operating temperature of the acetylene hydrogenation unit 50 may include, but are not limited to, the type of hydrogenation catalyst, the age/activity of the hydrogenation catalyst, flow rate, inlet acetylene concentration, CO concentration, presence of contaminants or poisons, other factors, or combinations of these. The acetylene hydrogenation unit 50 may operate at a pressure of from 100 pounds per square inch gauge (psig) to 1000 psig (i.e., about 690 kilopascals (kPa) to about 6900 kPa). The acetylene hydrogenation unit 50 may additionally operate at a gas hourly space velocity (GHSV) of from 1,000 to 14,000 (volume per volume of catalyst per hour).

When operating under normal operation conditions, a conversion of acetylene in the first hydrogenation reactor 150 of the acetylene hydrogenation unit 50 may be sufficient to maintain a concentration of acetylene in the hydrogenated effluent 52 less than or equal to the threshold acetylene concentration. In some embodiments, the acetylene conversion in the first hydrogenation reactor 150 may be greater than or equal to 85% under normal operation conditions, such as greater than or equal to 88%, greater than or equal to 90%, or even greater than or equal to 95%. Normal operation conditions refer to operation of the acetylene hydrogenation unit 50 at steady state with the acetylene concentration in the hydrogenated effluent 52 less than or equal to the threshold acetylene concentration. In some embodiments, under normal operation conditions, the acetylene conversion in the first hydrogenation reactor 150 may be from 85% to 95%, or from 88% to 92%.

The hydrogenated effluent 52 may refer to the effluents or compositions passed out of the acetylene hydrogenation unit 50, such as out of the last hydrogenation reactor of the acetylene hydrogenation unit 50. The hydrogenated effluent 52 may have an acetylene concentration less than the acetylene concentration of the hydrogenation feed 42. The hydrogenated effluent 52 may have an acetylene concentration of less than or equal to a threshold acetylene concentration, which may be specified by the olefin product user. In some embodiments, the hydrogenated effluent 52 may have an acetylene concentration of less than or equal to 2 part per million by volume (ppmv), less than or equal to 1 ppmv, less than or equal to 0.5 ppmv, or even less than or equal to 0.1 ppmv. The hydrogenation reaction in the acetylene hydrogenation unit 50 may consume hydrogen from the hydrogenation feed 42, but the change in concentration of hydrogen in the hydrogenated effluent 52 compared to the hydrogenation feed 42 may be less than the measurement uncertainty of analytical instruments due to the small concentrations of acetylene relative to the concentration of hydrogen in the hydrogenation feed 42. The hydrogenation catalyst and operating conditions of the acetylene hydrogenation unit 50 may be selective for hydrogenating acetylene relative to hydrogenation of product compounds, such as propylene and ethylene, produced in the steam cracking system 20 and/or the FCDh system 30.

Referring again to FIG. 4, the effluent processing system 38 may include a heat exchanger 60 disposed between the separation system 40 and the acetylene hydrogenation unit 50. The heat exchanger 60 may include the bypass 62 having a control valve 64. The temperature of the hydrogenation feed 42 at the inlet of the acetylene hydrogenation unit 50 may be increased or decreased by controlling the amount of the hydrogenation feed 42 passing through the heat exchanger 60 and the amount of the hydrogenation feed 42 bypassing the heat exchanger 60 through the bypass 62. Controlling an amount of the hydrogenation feed 42 bypassed around the heat exchanger 60 may allow for increasing or decreasing the temperature of the hydrogenation feed 42 at the inlet of the acetylene hydrogenation unit 50. The heat exchanger 60 for the hydrogenation feed 42 may be any type of heat exchanger known in the chemical industry.

In some embodiments, the effluent processing system 38 may include an acid gas removal process (not shown) downstream of the separation system 40. The acid gas removal process may be operable to remove acid gases from the hydrogenation feed 42, such as through scrubbing, upstream of the acetylene hydrogenation unit 50. In some embodiments, the acid gas removal process may be disposed between the separation system 40 and the heat exchanger 60. As previously discussed, in some embodiments, the acid gas removal process may be disposed upstream of the separation system 40.

The hydrogenated effluent 52 may be passed to one or more unit operations and/or processes downstream of the acetylene hydrogenation unit 50 for further processing of the hydrogenated effluent 52. Downstream processes may include vapor compression, separation, drying, or other operations and processes. The unit operations and processes downstream of the acetylene hydrogenation unit 50 may, ultimately, separate the hydrogenated effluent 52 into a plurality of gaseous streams, such as, but not limited to, an ethylene product stream, a propylene product stream, a propane stream, other streams, or combinations of these streams. One or more of these product streams may be passed as reactants or raw materials to further production processes, such as polymer production processes.

Figure 5:
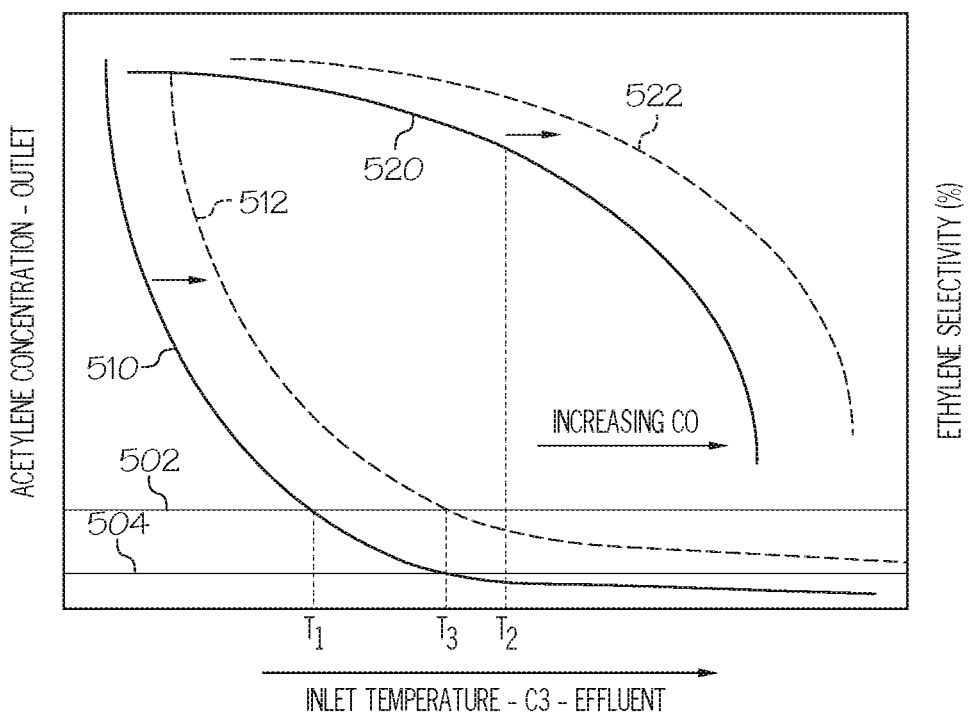
FIG. 5 graphically depicts a concentration of acetylene (y-axis-left) and an ethylene selectivity (y-axis-right) for an acetylene hydrogenation unit as a function of a temperature (x-axis) of a hydrogenation feed passed to the acetylene hydrogenation unit, according to one or more embodiments shown and described herein.

Referring now to FIG. 5, the acetylene concentration in the hydrogenated effluent 52 (y-axis left) and the ethylene selectivity of the acetylene hydrogenation unit 50 (y-axis right) are depicted as functions of the temperature (x-axis) of the hydrogenation feed 42 at the inlet to the acetylene hydrogenation unit 50. Line 502 in FIG. 5 represents a threshold acetylene concentration for the hydrogenated effluent 52, below which the concentration the acetylene is considered reduced to a level sufficient to satisfy the requirements of olefin users and/or to prevent or reduce fouling of catalysts, out-of-specification product streams, or other issues in downstream processes. As shown in FIG. 5, the acetylene concentration (curve 510) in the hydrogenated effluent 52 decreases with increasing inlet temperature for a given composition of the hydrogenation feed 42. FIG. 5 shows that the acetylene concentration 510 in the hydrogenated effluent 52 can be increased or decreased by decreasing or increasing, respectively, the inlet temperature to the acetylene hydrogenation unit 50. Temperature $T_1$ for the given composition of the hydrogenation feed 42 for curve 510 can be defined as the lowest temperature at which the acetylene concentration in the hydrogenated effluent 52 is equal to or less than the threshold acetylene concentration 502. At temperatures of the hydrogenation feed 42 greater than $T_1$ the acetylene concentration (510) in the hydrogenated effluent 52 is less than the threshold acetylene concentration. For temperatures of the hydrogenation feed 42 less than $T_1$, the acetylene concentration (510) in the hydrogenated effluent 52 may be greater than the threshold acetylene concentration. At temperatures less than $T_1$, the greater concentration of acetylene in the hydrogenated effluent 52 may lead to breakthrough of acetylene to downstream processes.

FIG. 5 also shows the ethylene selectivity of the acetylene hydrogenation unit 50 (curve 520) as a function of inlet temperature for the same composition of the hydrogenation feed 42 as curve 510. As shown in FIG. 5, the ethylene selectivity (curve 520) decreases with increasing inlet temperature. Thus, as the inlet temperature to the acetylene hydrogenation unit 50 increases, the ethylene selectivity of the acetylene hydrogenation unit 50 decreases, indicating that more acetylene and/or even some ethylene is converted to ethane, which may be caused by increased hydrogenation of ethylene in the acetylene hydrogenation unit 50. Increased hydrogenation of ethylene may lead to thermal runaway. For example, at temperatures of the hydrogenation feed 42 greater than temperature $T_2$, the ethylene selectivity may decrease to a point at which an unacceptable amount of ethylene undergoes hydrogenation. Since the ethylene hydrogenation reaction is exothermic, additional heat from the increased hydrogenation of ethylene and other olefins is released and may further increase the temperature in the acetylene hydrogenation unit 50, which further shifts the hydrogenation reaction towards hydrogenation of ethylene and propylene. The increasing heat generated from increasing hydrogenation of ethylene and other olefins may lead to thermal runaway of the acetylene hydrogenation unit 50. Thermal runaway can result in increased loss of olefin products through over-hydrogenation of the ethylene and propylene. Additionally, the increased temperatures in excess of 200° C. experienced during thermal runaway can damage the hydrogenation catalyst and equipment, such as reactors, instruments, heat exchangers, and other equipment, and may increase safety risks.

Referring again to FIG. 5, an operating window for the inlet temperature of the hydrogenation feed 42 introduced to the acetylene hydrogenation unit 50 for a given composition of the hydrogenation feed 42 can be defined between the inlet temperature $T_1$, below which the acetylene concentration in the hydrogenated effluent 52 is greater than the threshold acetylene concentration 502, and the inlet temperature $T_2$, above which the ethylene selectivity decreases and hydrogenation of olefin products can result in thermal runaway of the acetylene hydrogenation unit 50.

Changes in the composition of the hydrogenation feed 42 may change the operating window of the acetylene hydrogenation unit 50. In particular, changes in the concentration of hydrogen, CO, or both in the hydrogenation feed 42 may change the operating window of the acetylene hydrogenation unit 50. For example, referring again to FIG. 5, the process window for operation of the acetylene hydrogenation unit 50 can change in response to changes in the CO concentration in the hydrogenation feed 42. Increasing the CO concentration in the hydrogenation feed 42 may shift the process window for the temperature of the hydrogenation feed 42 towards greater temperatures and may widen the process window and. In FIG. 5, curve 512 represents the acetylene concentration in the hydrogenated effluent 52 as a function of inlet temperature of the hydrogenation feed 42 for operation of the acetylene hydrogenation unit 50 with an increased concentration of CO compared to the concentration of CO for curve 510. At a given temperature, increasing the concentration of CO reduces the conversion of acetylene. Not intending to be bound by any particular theory, it is believed that CO may interact with the hydrogenation catalyst in the hydrogenation unit to decrease the activity of the hydrogenation catalyst for hydrogenating acetylene. By increasing the concentration of CO in the acetylene hydrogenation unit 50, the inlet temperature $T_3$ of the hydrogenation feed 42 at which the acetylene concentration in the hydrogenated effluent 52 is equal to the threshold acetylene concentration 502 is greater than the corresponding temperature $T_1$ of the hydrogenation feed 42 for curve 510 (having a lesser concentration of CO). Thus, increasing the CO concentration in the hydrogenation feed 42 may result in the temperature of the hydrogenation feed 42 to be increased to maintain the concentration of acetylene in the hydrogenated effluent 52 less than the threshold acetylene concentration 502.

Increasing the CO concentration in the acetylene hydrogenation unit 50 may also shift the process window with respect to ethylene selectivity. Referring to FIG. 5, curve 522 represents the ethylene selectivity for the acetylene hydrogenation unit 50 as a function of time for a greater CO concentration compared to the CO concentration for curve 520. As shown in FIG. 5, increasing the CO concentration (curve 522) in the acetylene hydrogenation unit 50 can increase the ethylene selectivity at a given temperature. This may enable operation of the acetylene hydrogenation unit 50 at greater inlet temperatures compared to operating the acetylene hydrogenation unit 50 with a lesser concentration of CO. Thus, increasing the CO concentration in the acetylene hydrogenation unit 50 can enable operation of the acetylene hydrogenation unit 50 at a greater temperature without causing thermal runaway. Conversely, decreasing the concentration of CO in the acetylene hydrogenation unit 50 may decrease the ethylene selectivity at a given temperature, which may result in thermal runaway.

Referring again to FIG. 1, the steam cracking system 20 and the FCDh system 30 may be integrated to share a common effluent processing system 38, which may include at least the separation system 40 and acetylene hydrogenation unit 50. The steam cracking system 20 can be operated and the cracked gas 28 passed to the effluent processing system 38. Once the steam cracking system 20 and effluent processing system 38 are operating under normal conditions, the FCDh effluent 34 from the FCDh system 30 may be integrated into the effluent processing system 38 by introducing at least a portion of the FCDh effluent 34 to the separation system 40, combining the portion of the FCDh effluent 34 with the cracked gas 28 upstream of the separation system 40, or both. In some embodiments, the entire FCDh effluent 34 may be introduced to the separation system 40, combined with the cracked gas 28, or both. In some embodiments, only a portion of the FCDh effluent 34 may be introduced to the separation system 40, combined with the cracked gas 28, or both. The remaining FCDh effluent may be recycled back to the FCDh system 30 or back into combination with the second hydrocarbon feed 32 via FCDh effluent recycle 36. Additionally, in some embodiments, the portion of the FCDh effluent 34 introduced to the separation system 40, combined with the cracked gas 28, or both, may be a second portion of the FCDh effluent supplementing a first portion of the FCDh effluent already being integrated into the effluent processing system 38.

As previously discussed, the concentration of CO in the FCDh effluent 34 may be greater than the concentration of CO in the cracked gas 28. The cracked gas 28 may have a concentration of CO of from 50 ppmv to 400 ppmv. The FCDh effluent 34 may have a concentration of CO of from 600 ppmv to 2400 ppmv, such as from 1000 ppmv to 2000 ppmv. Increasing the amount of the FCDh effluent 34 introduced to the separation system 40, combined with the cracked gas 28, or both, may increase the concentration of CO in the hydrogenation feed 42 passed from the separation system 40 to acetylene hydrogenation unit 50.

As previously discussed, increasing the concentration of CO in the hydrogenation feed 42, which increases the CO concentration in the acetylene hydrogenation unit 50, may decrease the conversion of acetylene in the acetylene hydrogenation unit 50. Not intending to be bound by any particular theory, it is believed that the CO interacts with the hydrogenation catalyst to reduce the activity of the catalyst. The increased concentration of CO due to the FCDh effluent 34 may reduce the reaction rate, independent of temperature, of the hydrogenation reaction of acetylene, resulting in the decreased conversion of acetylene. In other words, at any given fixed reaction temperature, increasing the CO concentration may reduce the reaction rate of the hydrogenation reaction. Integration of the FCDh effluent 34 may also increase the mass flow rate of the hydrogenation feed 42 and mass flow rate through the acetylene hydrogenation unit 50, which may also operate to reduce the conversion of acetylene in the acetylene hydrogenation unit 50. The decreased conversion of acetylene can lead to an increase in the concentration of acetylene in the hydrogenated effluent 52 above the threshold acetylene concentration. The increased concentration of acetylene in the hydrogenated effluent 52 can lead to breakthrough of acetylene to downstream separation and purification processes and/or out-of-specification product streams.

The methods disclosed herein for operating the acetylene hydrogenation unit 50 when integrating a portion of an FCDh system 30 with a steam cracking system 20 may reduce or prevent concentrations of acetylene in the hydrogenated effluent 52 greater than the threshold acetylene concentration by increasing the acetylene conversion in the first hydrogenation reactor 150 of the acetylene hydrogenation unit 50 above a threshold acetylene conversion prior to introducing the FCDh effluent 34 to the separation system 40, combining the FCDh effluent 34 with the cracked gas 28, or both. As used herein, the "threshold acetylene conversion" may refer to a minimum acetylene conversion in the first hydrogenation reactor 150, before integration of the portion of the FCDh effluent 34, above which the acetylene concentration in the hydrogenated effluent 52 is maintained less than or equal to the threshold acetylene concentration during and/or after integrating the portion of the FCDh effluent 34. Thus, when the acetylene conversion in the first hydrogenation reactor 150 is greater than or equal to the threshold acetylene conversion, introducing the FCDh effluent 34 to the effluent processing system 38 will not cause the acetylene concentration in the hydrogenated effluent 52 to increase above the threshold acetylene concentration.

The acetylene conversion in the first hydrogenation reactor 150 may be increased above the threshold acetylene concentration by increasing the temperature of the acetylene hydrogenation unit 50, such as by increasing the temperature of the hydrogenation feed 42 before passing the hydrogenation feed 42 to the acetylene hydrogenation unit 50. By increasing the acetylene conversion in the first hydrogenation reactor 150 above the threshold acetylene conversion immediately prior to integrating the portion of the FCDh effluent 34, the resulting decrease in acetylene conversion caused by the increase in CO concentration from introducing the portion of the FCDh effluent 34 may be accommodated by the acetylene hydrogenation unit 50 without the concentration of acetylene in the hydrogenated effluent 52 increasing to a level greater than the threshold acetylene concentration. In other words, the acetylene conversion is increased prior to integration of the FCDh effluent 34 so that when the FCDh effluent 34 is integrated, the increase in CO concentration does not result in the acetylene concentration in the hydrogenated effluent 52 exceeding the threshold acetylene concentration.

Referring again to FIG. 5, the curve 510 may represent a normal operation of the acetylene hydrogenation unit 50 when only the cracked gas 28 is passed to the separation system 40. For curve 510, operating the acetylene hydrogenation unit 50 at a temperature greater than or equal to $T_1$ may result in the acetylene concentration in the hydrogenated effluent 52 being less than the threshold acetylene concentration 502. However, when the CO concentration in the acetylene hydrogenation unit 50 increases due to the integration of a portion of the FCDh effluent 34, such as with curve 512, the acetylene concentration in the hydrogenated effluent 52 at temperature $T_1$ may be greater than the threshold acetylene concentration 502. As previously discussed, the acetylene conversion in the first hydrogenation reactor 150 can be increase by increasing the temperature of the first hydrogenation reactor 150, such as by increasing a temperature of the hydrogenation feed 42. During normal operation (curve 510), increasing the temperature of the acetylene hydrogenation unit 50 to a temperature greater than or equal to $T_3$ may increase the acetylene conversion, thereby decreasing the acetylene concentration in the hydrogenated effluent 52 well below the threshold acetylene concentration 502.

With the acetylene hydrogenation unit 50 operating at a temperature greater than or equal to $T_3$, introducing a portion of the FCDh effluent 34 may increase the concentration of CO in acetylene hydrogenation unit 50, which may shift operation of the acetylene hydrogenation unit 50 the right in FIG. 5 to curve 512. As shown in FIG. 5, at temperatures greater than or equal to $T_3$, the acetylene concentration in the hydrogenated effluent 52 may increase but may still be maintained below the threshold acetylene concentration 502 due to the increased acetylene conversion in the first hydrogenation reactor 150 prior to introducing the portion of the FCDh effluent 34.

Referring again to FIG. 1, the threshold acetylene conversion in the first hydrogenation reactor 150 may depend on the relative size of the FCDh system 30 compared to the steam cracking system 20. The relative size of the FCDh system 30 to the steam cracking system 20 in the may be characterized by a flow ratio. As used herein, the "flow ratio" may be a ratio of the mass flow rate of a portion of the hydrogenation feed 42 contributed by the FCDh effluent 34 divided by a mass flow rate of a portion of the hydrogenation feed 42 contributed by the cracked gas 28. In some embodiments in which the effluent processing system 38 has an FEDP configuration, the flow ratio may be equivalent to the mass flow rate of C3 and C3− constituents in the portion of the FCDh effluent 34 passed to the separator 40 divided by the mass flow rate of the C3 and C3− constituents in the cracked gas 28, where the mass flow rate of the C3 and C3− constituents in a stream is equal to the total mass flow rate of the stream multiplied by the mass fraction of C3 and C3− constituents in the stream. In embodiments in which the effluent processing system 38 has an FEDE configuration, the flow ratio may be equivalent to the mass flow rate of C2 and C2− constituents in the portion of the FCDh effluent 34 passed to the separator 40 divided by the mass flow rate of the C2 and C2− constituents in the cracked gas 28, where the mass flow rate of the C2 and C2− constituents in a stream is equal to the total mass flow rate of the stream multiplied by the mass fraction of the C2 and C2− constituents in the stream. The flow ratio for the integrated process 10 for producing olefins may be less than or equal to 1/2, less than or equal to 1/4, less than or equal to 1/8, or less than or equal to 1/12. The threshold acetylene conversion in the first hydrogenation reactor 150 may also depend on whether the separation system 40 of the effluent processing system 38 has a front-end depropanizer (FEDP) or a front-end de-ethanizer (FEDE) configuration (e.g., whether or not the C3 compounds are in the hydrogenation feed 42).

When the separation system 40 is a front-end depropanizer (FEDP configuration) and the flow ratio is less than or equal to 1/12, the threshold acetylene conversion in the first hydrogenation reactor 150 may be greater than or equal to 0.95, greater than or equal to 0.96, or even greater than or equal to 0.97, wherein the flow ratio is as previously defined herein. When the separation system 40 is a front-end depropanizer and the flow ratio is from 1/12 to 1/2, the threshold acetylene conversion in the first hydrogenation reactor 150 may be calculated from the following Equation 1 (EQU. 1):

$$\text{Min}[(-0.00024 \times C_{CO} + (0.5 \times R) + 0.942), 0.99] \qquad \text{EQU. 1}$$

In EQU. 1, $C_{CO}$ is a carbon monoxide concentration in the hydrogenation feed 42 contributed by the cracked gas 28 in parts per million by volume of the hydrogenation feed, and R is the flow ratio. In other words, when the flow ratio is from 1/12 to 1/2 for an FEDP configuration, the threshold acetylene conversion is the lesser of 0.99 or the value calculated from the expression $(-0.00024 \times C_{CO} + (0.5 \times R) + 0.942)$.

When the separation system 40 is a front-end de-ethanizer (FEDE configuration) and the flow ratio is less than or equal to 1/2, the threshold acetylene conversion may be greater than or equal to 0.99, greater than or equal to 0.995, or even greater than or equal to 0.999, wherein the flow ratio is as previously described.

Referring to FIG. 1, a method for operating the acetylene hydrogenation unit 50 of the integrated process 10 for producing olefins that includes the steam cracking system 20 that integrates at least a portion of the FCDh effluent 34 from the FCDh system 30 will now be described. The method may include cracking at least a portion of the first hydrocarbon feed 22 in the steam cracking system 20 to produce a cracked gas 28. The first hydrocarbon feed 22, steam cracking system 20, and cracked gas 28 may have any of the features or characteristics previously described herein for the first hydrocarbon feed 22, the steam cracking system 20, or the cracked gas 28, respectively. The method may further include separating the cracked gas 28 into at least the hydrogenation feed 42 and the acetylene-depleted stream 44 in a separation system 40. The hydrogenation feed 42 may include at least acetylene, carbon monoxide, hydrogen, and at least one product. The hydrogenation feed 42 may include any other composition previously described herein for the hydrogenation feed 42. The method may further include dehydrogenating at least a portion of the second hydrocarbon feed 32 in the FCDh system 30 to produce the FCDh effluent 34. The FCDh effluent 34 may include a concentration of carbon monoxide greater than a concentration of carbon monoxide in the cracked gas 28. The second hydrocarbon feed 32, the FCDh system 30, and the FCDh effluent 34 may have any of the features, characteristics, or properties previously described herein for the second hydrocarbon feed 32, the FCDh system 30, and the FCDh effluent 34, respectively. The method may further include introducing at least a portion of the FCDh effluent 34 to the separation system 40, combining at least a portion of the FCDh effluent 34 with the cracked gas 28 upstream of the separation system 40, or both. Introducing the portion of the FCDh effluent 34 to the separation system 40, combining the portion of the FCDh effluent 34 with the cracked gas 28, or both, may increase a concentration of carbon monoxide in the hydrogenation feed 42. The method may further include contacting the hydrogenation feed 42 with an acetylene hydrogenation catalyst in the acetylene hydrogenation unit 50, the contacting causing hydrogenation of at least a portion of the acetylene in the hydrogenation feed 42 to produce the hydrogenated effluent 52. The hydrogenation feed 42, the acetylene hydrogenation unit 50, and the hydrogenated effluent 52 may have any of the features, properties, or characteristics previously described herein for the hydrogenation feed 42, the acetylene hydrogenation unit 50, and the hydrogenated effluent 52, respectively. An elevated concentration of CO in the hydrogenation feed 42 due to the portion of the FCDh effluent 34 may reduce the reaction rate, independent of temperature, of the hydrogenation of the acetylene. The acetylene hydrogenation unit 50 may operate at an elevated temperature relative to normal operating temperatures when the portion of the FCDh effluent 34 is not introduced to the separation system 40, combined with the cracked gas 28, or both, such that a concentration of acetylene in the hydrogenated effluent 52 may be less than the threshold acetylene concentration.

In some embodiments of the previously described method, the concentration of acetylene in the hydrogenated effluent may not increase above the threshold acetylene concentration during introducing the portion of the FCDh effluent to the separation system, combining the portion of the FCDh effluent with the cracked gas, or both. In any of the previously described methods, the threshold acetylene concentration may be less than or equal to 2.0 ppmv, or less than or equal to 1.0 ppmv.

In some embodiments of the previously described methods, the acetylene hydrogenation unit 50 may include at least the first hydrogenation reactor 150 and the second hydrogenation reactor 160 downstream of the first hydrogenation reactor 150, and the elevated temperature of the acetylene hydrogenation unit 50 may be sufficient to increase an acetylene conversion in the first hydrogenation reactor 150, immediately prior to integrating the portion of the FCDh effluent 34, to greater than a threshold acetylene conversion, the threshold acetylene conversion being a minimum acetylene conversion in the first hydrogenation reactor, before integration of the portion of the FCDh effluent, above which the acetylene concentration in the hydrogenated effluent is maintained less than or equal to the threshold acetylene concentration after integrating the portion of the FCDh effluent. In some embodiments, the separation system 40 may be a front end depropanizer (FEDP), and the threshold acetylene conversion in the first hydrogenation reactor 150 may be greater than or equal to 0.95 for a flow ratio of less than or equal to 1/12, the flow ratio being previously defined herein. In some embodiments, the separation system 40 may be a front end depropanizer, a flow ratio may be from 1/12 to 1/2, and the threshold acetylene conversion in the first hydrogenation reactor 150 may be greater than or equal to the value determined from EQU. 1:

$$\text{Min}[(-0.00024 \times C_{CO} + (0.5 \times R) + 0.942), 0.99]$$ EQU. 1 where $C_{CO}$ is a carbon monoxide concentration in the hydrogenation feed 42 contributed by the cracked gas in parts per million by volume of the hydrogenation feed and R is the flow ratio. In some embodiments, the separation system 40 may be a front end de-ethanizer (FEDE), and the threshold acetylene conversion in the first hydrogenation reactor 150 may be greater than or equal to 0.99 for a flow ratio less than or equal to 1/2.

Any embodiments of the methods disclosed herein may also additionally include returning the acetylene hydrogenation unit 50 to normal operating conditions, in which the acetylene conversion in the first hydrogenation reactor 150 is maintained in a range of from 85% to 95%, or from 88% to 92%, after integrating the portion of the FCDh effluent 34 into the separation system 40 and acetylene hydrogenation unit 50. The acetylene hydrogenation unit 50 may be returned to normal operating conditions by increasing or decreasing the temperature of the hydrogenation feed 42, increasing or decreasing an amount of CO produced in the steam cracking system 20, or both, to adjust the operating conditions of the acetylene hydrogenation unit 50.

In some embodiments, the FCDh effluent 34 may be progressively introduced to the separation system 40, combined with the cracked gas 28, or both, in discrete portions less than the entire FCDh effluent stream 34. In some embodiments, the FCDh effluent 34 may be progressively integrated into the separation system 40 when the flow ratio is greater than about 1/12. As each discrete portion of the FCDh effluent 34 is introduced to the separation system 40, combined with the cracked gas 28, or both, the remaining portions of the FCDh effluent 34 may be recycled through the FCDh effluent recycle 36 back to the FCDh system 30 or back into combination with the second hydrocarbon feed 32 upstream of the FCDh system 30. Any of the methods disclosed herein may include introducing a first portion of the FCDh effluent 34 to the separation system 40, combining the first portion of the FCDh effluent 34 with the cracked gas 28 upstream of the separation system 40, or both, wherein introducing the first portion of the FCDh effluent 34 to the separation system 40, combining the first portion of the FCDh effluent 34 with the cracked gas 28, or both, increases the concentration of CO in the hydrogenation feed 42 and reduces the conversion of acetylene in the acetylene hydrogenation unit 50.

The methods may further include recycling the remaining portions of the FCDh effluent 34 back to the FCDh system 30 through FCDh effluent recycle 36. The methods may include increasing the temperature of the acetylene hydrogenation unit 50 to increase the conversion of acetylene in the acetylene hydrogenation unit 50, such as in the first hydrogenation reactor 150 of the acetylene hydrogenation unit 50, to greater than a threshold acetylene conversion. The temperature of the acetylene hydrogenation unit 50 may be increased by increasing the temperature of the hydrogenation feed 42 passed to the acetylene hydrogenation unit 50. The methods may further include passing at least a second portion of the FCDh effluent 34 to the separation system 40, combining at least a second portion of the FCDh effluent 34 with the cracked gas 28 and the first portion of the FCDh effluent 34 upstream of the separation system 40, or both, wherein integrating the at least a second portion of the FCDh effluent 34 further increases the CO concentration in the hydrogenation feed 42 and further reduces the conversion of acetylene in the acetylene hydrogenation unit 50. Additional portions of the FCDh effluent 34, such as a third portion, fourth portion, fifth portion, and other portions, may also be integrated into the separation system 40 and acetylene hydrogenation unit 50, each portion of the FCDh effluent 34 being preceded by a step of increasing the acetylene conversion in the first hydrogenation reactor 150. In some embodiments, the mass flow rate of the portion of the hydrogenation feed 42 contributed by the FCDh effluent 34 may be greater than 0% and less than or equal to 12% of the mass flow rate of the portion of the hydrogenation feed 42 contributed by the cracked gas 28. In some embodiments, the mass flow rate of the portion of the hydrogenation feed 42 contributed by the FCDh effluent 34 may be from 4% to 12% or from 4% to 8% of the mass flow rate of the portion of the hydrogenation feed 42 contributed by the cracked gas 28.

Alternatively or additionally, in some embodiments, the mass flow rate of C3 and C3− constituents in the portion of the FCDh effluent 34 passed to the separator 40 may be greater than 0% and less than or equal to 12% of the mass flow rate of the C3 and C3− constituents in the cracked gas 28 for an effluent processing system 38 having an FEDP configuration. In some embodiments, the mass flow rate of C3 and C3− constituents in the portion of the FCDh effluent 34 passed to the separator 40 may be from 4% to 12% or even from 4% to 8% of the mass flow rate of the C3 and C3− constituents in the cracked gas 28 for an effluent processing system 38 having an FEDP configuration. In some embodiments, the mass flow rate of C2 and C2− constituents in the portion of the FCDh effluent 34 passed to the separator 40 may be greater than 0% and less than or equal to 12% of the mass flow rate of the C2 and C2− constituents in the cracked gas 28 for an effluent processing system 38 having an FEDE configuration. In some embodiments, the mass flow rate of C2 and C2− constituents in the portion of the FCDh effluent 34 passed to the separator 40 may be from 4% to 12% or even from 4% to 8% of the mass flow rate of the C2 and C2− constituents in the cracked gas 28 for an effluent processing system 38 having an FEDE configuration.

In some embodiments, the method may include cracking at least a portion of the first hydrocarbon feed 22 in the steam cracking system 20 to produce the cracked gas 28 and separating the cracked gas 28 into at least the hydrogenation feed 42 and the acetylene-depleted stream 44 in the separation system 40. The first hydrocarbon feed 22, steam cracking system 20, cracked gas 28, separation system 40, and hydrogenation feed 42 may have any of the features, properties, or characteristics previously described herein for the first hydrocarbon feed 22, the steam cracking system 20, the cracked gas 28, the separation system 40, or the hydrogenation feed 42, respectively. The hydrogenation feed 42 may include at least acetylene, CO, hydrogen, and at least one product. The method may further include contacting the hydrogenation feed 42 with the acetylene hydrogenation catalyst in the acetylene hydrogenation unit 50 that includes at least the first hydrogenation reactor 150 and the second hydrogenation reactor 160, the contacting causing hydrogenation of at least a portion of the acetylene in the hydrogenation feed 42 to produce the hydrogenated effluent 52. The methods may further include increasing the temperature of the hydrogenation feed 42 such that the conversion of acetylene in the first hydrogenation reactor 150 is greater than or equal to the threshold acetylene conversion, the threshold acetylene conversion being a minimum acetylene conversion in the first hydrogenation reactor 150, before integration of the portion of the FCDh effluent 34, above which the acetylene concentration in the hydrogenated effluent 52 is maintained less than or equal to the threshold acetylene concentration after integrating the portion of the FCDh effluent 34. The methods may include dehydrogenating at least a portion of the second hydrocarbon feed 32 in the FCDh system 30 to produce the FCDh effluent 34, the FCDh effluent 34 having a concentration of CO greater than a concentration of CO in the cracked gas 28. The second hydrocarbon feed 32, the FCDh system 30, and the FCDh effluent 34 may have any of the features, characteristics, or properties previously described herein for the second hydrocarbon feed 32, the FCDh system 30, and the FCDh effluent 34, respectively. The methods may further include introducing at least a portion of the FCDh effluent 34 to the separation system 40, combining at least a portion of the FCDh effluent 34 with the cracked gas 28 upstream of the separation system 40, or both, wherein introducing the portion of the FCDh effluent 34 to the separation system 40, combining the portion of the FCDh effluent 34 with the cracked gas 28, or both, increases a concentration of CO in the hydrogenation feed 42. The elevated concentration of CO in the hydrogenation feed 42 due to the portion of the FCDh effluent 34 may reduce a reaction rate, independent of temperature, of the hydrogenation of the acetylene. The elevated temperature of the acetylene hydrogenation unit 50 relative to normal operating temperatures when the portion of the FCDh effluent 34 is not introduced to the separation system 40, combined with the cracked gas 28, or both, may maintain the concentration of acetylene in the hydrogenated effluent 52 less than or equal to the threshold acetylene concentration.

In some embodiments, the concentration of acetylene in the hydrogenated effluent 52 may not increase above the threshold acetylene concentration during introducing the portion of the FCDh effluent 34 to the separation system 40, combining the portion of the FCDh effluent 34 with the cracked gas 28, or both. In any of the previously described methods, the threshold acetylene concentration may be less than or equal to 2.0 ppmv, or less than or equal to 1.0 ppmv.

In some embodiments, the separation system 40 may be a front end depropanizer, and the threshold acetylene conversion in the first hydrogenation reactor 150 may be greater than or equal to 0.95 for a flow ratio of less than or equal to 1/12, the flow ratio being previously defined herein. In some embodiments, the separation system 40 may be a front end depropanizer, a flow ratio may be from 1/12 to 1/2, and the threshold acetylene conversion in the first hydrogenation reactor 150 may be greater than or equal to the value determined from EQU. 1:

$$\min[-0.00024 \times C_{CO}+(0.5 \times R)+0.942, 0.99] \qquad \text{EQU. 1}$$

where $C_{CO}$ is a carbon monoxide concentration in the hydrogenation feed 42 contributed by the cracked gas in parts per million by volume of the hydrogenation feed and R is the flow ratio. In some embodiments, the separation system 40 may be a front end de-ethanizer, and the threshold acetylene conversion in the first hydrogenation reactor 150 may be greater than or equal to 0.99 for a flow ratio less than or equal to 1/2.

EXAMPLES

Embodiments of the present disclosure will be further clarified by the following examples, which should not be construed as limiting on the disclosed and/or claimed embodiments presently described.

Example 1: Production and Analysis of FCDh Effluent

In Example 1, an FCDh effluent was produced and analyzed for composition with respect to C3+ compounds and C3− compounds. The propane dehydrogenation was carried out in a modified Davison Circulating Riser (DCR) pilot unit, in which in-situ fuel combustion is carried out in the regeneration section. Approximately 4100 grams of a supported Ga—Pt catalyst was loaded in the circulating system and about 90 g of the catalyst was calculated to be in the reactor at any given time. The inlet temperature to the riser (reactor) was controlled at 630° C. and the pressure was set to a gauge pressure of 90 kilopascals (kPa) (13 psig or absolute pressure of 191 kPa/27.7 psia). High purity propane was injected into the system to achieve a weight hourly space velocity (WHSV) of propane around 3.5 per hour. Nitrogen ($N_2$) was co-fed into the system mostly as a carrier gas of catalyst. The partial pressure of propane was around a gauge pressure of about 30 kPa (4.3 psig). The temperature for catalyst regeneration ranged between 700° C. and 750° C. High purity methane ($CH_4$) was used as the fuel gas in the regenerator and was injected at rate of 50 standard liters per hour.

The reactor system was operated for a period of time sufficient to attain steady state operation, at which point samples of the FCDh effluent from the reactor system were collected and analyzed for composition using techniques known in the art. In particular, the FCDh effluents were analyzed to determine the concentrations of CO, carbon dioxide ($CO_2$), $C_2$ and $C_{2-}$ compounds (including hydrogen), and $C_3$ compounds. The results are provided below in Table 1.

TABLE 1

| Fuel Gas in Regenerator | High-purity $CH_4$ |
|---|---|
| CO (ppmv) | 1178 |
| $CO_2$ (ppmv) | 88 |
| $C_2$, $C_{2-}$, & $H_2$ (mol %) | 30.6 |
| $C_3$ (mol %) | 69.3 |

The data shows that the concentration of CO in the FCDh effluent can be much greater than the concentration of CO in a typical hydrogenation feed to the acetylene hydrogenation unit, the hydrogenation feed comprising only the cracked gas from a steam cracking system. The typical concentrations for CO in the hydrogenation feed when only the cracked gas is introduced to the separator is provided in Table 2 for a front end de-ethanizer (FEDE) configuration and a front end de-propanizer (FEDP) configuration. Additionally, concentration of acetylene in the FCDh effluent is less than 50 ppmv. This concentration of acetylene was, therefore, found to be orders of magnitude less than the concentration of acetylene in the feed stream to acetylene converter in a steam cracking system without integration of the FCDh system. The following Table 2 provides the typical concentrations of acetylene in the hydrogenation feed when only the cracked gas is introduced to the separator. Table 2 provides data for a front end de-ethanizer (FEDE) and a front end de-propanizer (FEDP) configuration.

TABLE 2

| Configuration | CO in Hydrogenation Feed (ppmv) | Acetylene in Hydrogenation Feed (ppmv) |
|---|---|---|
| FEDE | 50-200 | 1500-3000 |
| FEDP | 50-400 | 2000-5000 |

Example 2 Modeling of the Integration of FCDh and Steam Cracking

An empirical model well practiced for acetylene hydrogenation units is used for evaluating acetylene conversion changes in the acetylene hydrogenation unit when the FCDh effluent from the FCDh system and the cracked gas from the steam cracking system are combined. Investigations were carried out with respect to variations in the ratio of the FCDh effluent to cracked gas, the CO level in the cracked gas, conversion split among the individual acetylene hydrogenation reactors of the acetylene hydrogenation unit, and separation system configurations. In the empirical model, the CO concentration in the FCDh effluent was set at 1200 ppmv for convenience. The concentration of acetylene in the FCDh effluent was not included due to its ultra-low concentration.

The acetylene hydrogenation unit used in the model has a configuration of three hydrogenation reactors (A, B, C) in series, each of the hydrogenation reactors having equivalent reactor dimensions, which are typical for an FEDP process configuration. Reactor A (first hydrogenation reactor) carries out the majority of the acetylene conversion, and Reactor B finishes the rest of the conversion. Reactor C is in general a polishing bed to prevent the hydrogenated effluent from being out-of-specification for acetylene concentration. The threshold acetylene concentration in the hydrogenated effluent was set to be less than 1 ppmv. The acetylene conversion split among Reactor A, B, C are set at targeted values to determine the inlet temperatures. The composition used for the cracked gas from the steam cracker in the model is provided below in Table 3.

TABLE 3

| Feed Component | Concentration |
|---|---|
| Hydrogen (mol %) | 20 |
| CO (ppmv) | Variable* |
| $CO_2$ (mol %) | 0 |
| $CH_4$ (mol %) | 30.3 |
| Acetylene (ppmv) | 3000 |
| Ethylene ($C_2H_4$) (mol %) | 32.6 |
| Ethane ($C_2H_6$) (mol %) | 5.8 |
| Propylene ($C_3H_6$) (mol %) | 7.5 |
| Propane ($C_3H_8$) (mol %) | 3.5 |
| C4+ Compounds (mol %) | 0 |

*The concentration of CO in the cracked gas was varied from 50 ppmv to 300 ppmv in Example 2 and from 50 ppmv to 200 ppmv in the following Example 3.

The overall GHSV for acetylene hydrogenation unit is 5000 hr−1 without the FCDh effluent. The composition for the FCDh effluent in Example 1 is used as the composition for the FCDh effluent in the model prediction.

Before introducing the FCDh effluent, the acetylene hydrogenation unit is normally operated at a 90%:10% conversion split between the first hydrogenation reactor (Reactor A) and the second hydrogenation reactor (Reactor B) for a steam cracking system with FEDP configuration. A third hydrogenation reactor (Reactor C) may be present typically as a polishing bed. If FCDh system starts up and the FCDh effluent is introduced into combination with the cracked gas from the steam cracking system and the resulting hydrogenation feed is passed to the first hydrogenation reactor without adjusting operation conditions, the acetylene conversion in the first hydrogenation reactor will be decreased due to the higher CO concentration in the combined stream. If the conversion in the first hydrogenation reactor is below 85%, there is increased risks of producing out-of-specification ethylene with higher than desired acetylene concentration (e.g., breakthrough of acetylene from the acetylene hydrogenation unit). Therefore, the acetylene conversion in the first hydrogenation reactor is increased by increasing the inlet temperature of the hydrogenation feed before the introduction of the FCDh effluent into combination with the cracked gas to make sure acetylene conversion will be at least 85% for the combined product stream.

The modeling was first carried out with combined stream that included the C3 and C3− constituents of the cracked gas from the steam cracking system, which are provided in Table 3, and the C3 and C3− constituents of the FCDh effluent, which are provided in Table 1 in Example 1. The C3 and C3− cut in the combined stream is the hydrogenation feed of interest. The inlet temperature of the hydrogenation feed passed to the first hydrogenation reactor is determined in order to reach 85% acetylene conversion in the first hydrogenation reactor for the combined stream. The inlet temperatures for the second and third hydrogenation reactors are set at 2° C. less than inlet temperature of the first hydrogenation reactor. The same inlet temperatures of the hydrogenation feed for processing the combined stream are used to determine the safe operation conversion of acetylene in the first hydrogenation reactor (threshold acetylene conversion) for the cracked gas only case (hydrogenation feed coming from the steam cracking system only) before introducing the FCDh effluent.

Figure 6:
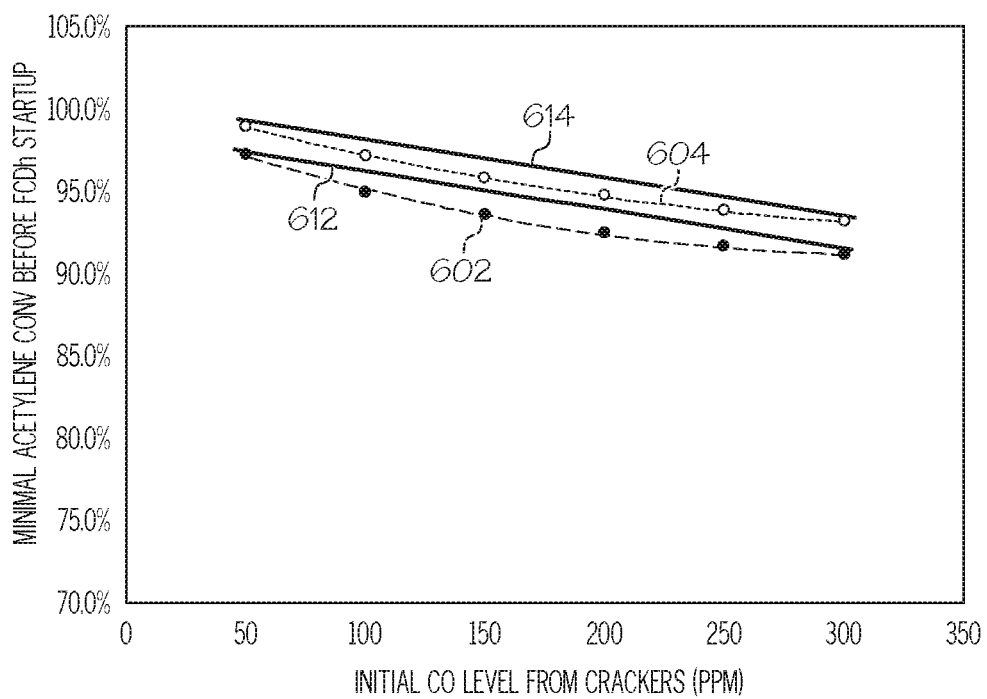
FIG. 6 graphically depicts a minimum acetylene conversion (y-axis) in a first hydrogenation reactor prior to integration of an FCDh effluent with a cracked gas as a function of the initial CO level in the hydrogenation feed contributed by the steam cracking unit (x-axis), where the minimum acetylene conversion is the acetylene conversion before integration of the FCDh effluent that results in 85% conversion of acetylene after integration of the FCDh effluent, according to one or more embodiments shown and described herein.

In Example 2, the minimal safe operation conversion of acetylene in the first hydrogenation reactor (threshold acetylene conversion) before introducing the FCDh effluent in order to achieve at least 85% acetylene conversion in the first hydrogenation reactor after introducing the FCDh effluent was determined for varying concentrations of CO in the cracked gas. The CO concentration was varied from 50 ppmv to 300 ppmv in 50 ppmv intervals. FIG. 6 shows the threshold acetylene conversion in the 1st hydrogenation reactor (y-axis) immediately before integration of the FCDh effluent that resulted in maintaining at least 85% acetylene conversion in the 1st hydrogenation reactor after integration of the FCDh effluent as a function of the CO concentration in the hydrogenation feed that is contributed by the cracked gas. Below 85% acetylene conversion, a high probability exists that acetylene may breakthrough to produce an out-of-specification ethylene product stream. In FIG. 6, data series 602 is the threshold acetylene conversion as a function of CO concentration in the hydrogenation feed contributed by the cracked gas for the flow rate of portion of the hydrogenation feed contributed by the FCDh effluent equal to 8% of the flow rate of the portion of the hydrogenation feed contributed from cracked gas by mass. Data series 604 is the threshold acetylene conversion as a function of CO concentration in the hydrogenation feed contributed by the cracked gas for the flow rate of the portion of the hydrogenation feed contributed by the FCDh effluent equal to 12% of the flow rate of the portion of the hydrogenation feed contributed from cracked gas by mass. In order to ensure there will be no out-of-specification ethylene after introducing the portion of FCDh effluent, the conversion of acetylene in the 1st hydrogenation reactor should be on or above the data series 602 in FIG. 6 for a flow ratio of 8%, or on or above data series 604 in FIG. 6 for a flow ratio of 12%. A straight line 612 can be drawn for which all points on line 612 are above data series 602 and a straight line 614 can be drawn for which all points on line 614 are above data series 604. Any points on line 612 or above line 612 will, therefore, always have an acetylene conversion in the first hydrogenation reactor greater than the threshold acetylene conversion for a flow ratio of 8% or less. Any points on line 614 or above line 614 will, therefore, always have an acetylene conversion in the first hydrogenation reactor greater than the threshold acetylene conversion for a flow ratio of 12% or less. For a given integrated FCDh-steam cracker system with flow ratio R<1/2, the required minimal acetylene conversion can be expressed by the simple linear relationship in EQU. 1, which is provided again below.

$$\text{Min}[(-0.00024 \times C_{CO} + (0.5 \times R) + 0.942), 0.99] \quad \text{EQU. 1}$$

where $C_{CO}$ is a carbon monoxide concentration in the hydrogenation feed 42 contributed by the cracked gas in parts per million by volume of the hydrogenation feed and R is the flow ratio. Therefore, the temperature of the acetylene hydrogenation unit can be increased to increase the acetylene conversion above the conversion calculated using EQU. 1. This increased acetylene conversion in the first hydrogenation reactor can ensure the acetylene conversion will stay above 85% after the portion of hydrogenation feed from the FCDh effluent smaller than 1/2 of the flow rate of hydrogenation feed from cracked gas is introduced to the separation system or combined with the cracked gas.

Example 3: Modeling of the Integration of FCDh and Steam Cracking in FEDE Configuration to Maintain the Acetylene Conversion in First Reactor Greater than 96.5%

Figure 7:
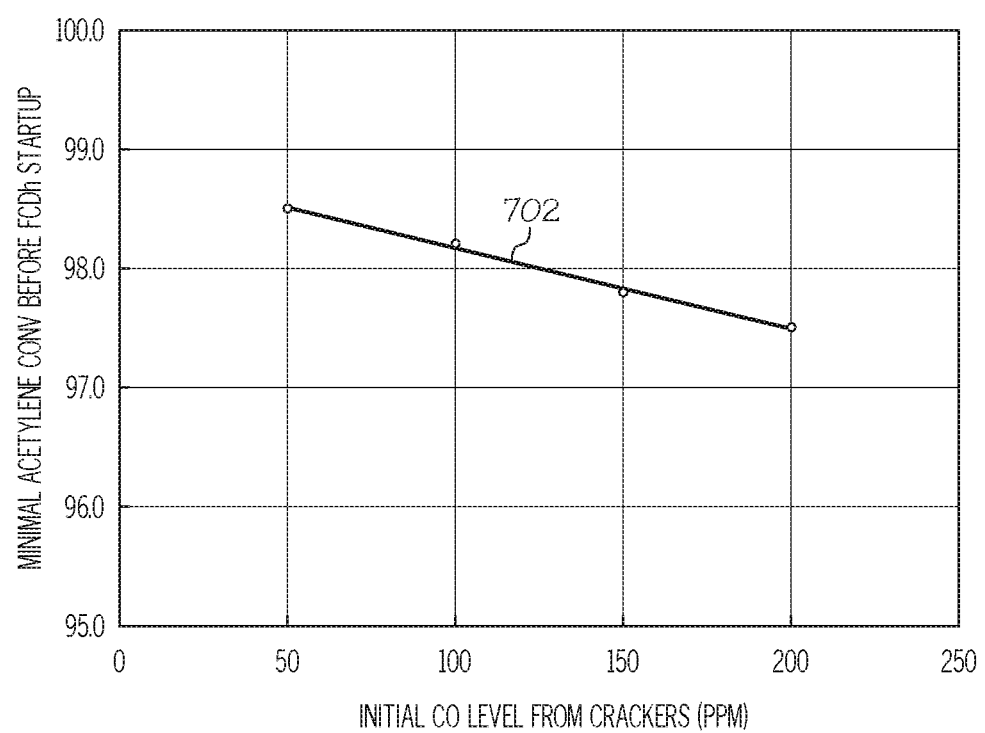
FIG. 7 graphically depicts a minimum acetylene conversion (y-axis) in a first hydrogenation reactor prior to integration of an FCDh effluent with a cracked gas as a function of the initial CO level in the hydrogenation feed contributed by the steam cracking unit (x-axis), where the minimum acetylene conversion is the acetylene conversion before integration of the FCDh effluent that results in 96.5% conversion of acetylene after integration of the FCDh effluent, according to one or more embodiments shown and described herein.

For Example 3, the integrated process for producing olefins that includes the FCDh system integrated with the steam cracking system with FEDE configuration was modeled for maintaining the acetylene conversion in the first hydrogenation reactor greater than 96.5% (a conversion below which there is high probability acetylene will breakthrough to make ethylene out of spec). The modeling was performed according to the process described in Example 2. For Example 3, the flow ratio R was equal to 4% for the FEDE configuration. Referring to FIG. 7, the threshold acetylene conversions in the first hydrogenation reactor that resulted in maintaining at least 96.5% acetylene conversion after integration of the FCDh effluent is provided as a function of the CO concentration contributed by the cracked gas in the hydrogenation feed. The results show in the CO range generally practiced, acetylene conversion in the first hydrogenation reactor is greater than or equal to 99% can ensure acetylene conversion maintaining at least 96.5% after integration of the FCDh effluent.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

Generally, "inlet ports" and "outlet ports" of any system unit of the integrated process 10 for producing olefins described herein refer to openings, holes, channels, apertures, gaps, or other like mechanical features in the system unit. For example, inlet ports allow for the entrance of materials to the particular system unit and outlet ports allow for the exit of materials from the particular system unit. Generally, an outlet port or inlet port will define the area of a system unit of the integrated process 10 to which a pipe, conduit, tube, hose, material transport line, or like mechanical feature is attached, or to a portion of the system unit to which another system unit is directly attached. While inlet ports and outlet ports may sometimes be described herein functionally in operation, they may have similar or identical physical characteristics, and their respective functions in an operational system should not be construed as limiting on their physical structures.

It will be apparent to those skilled in the art that various modifications and variations can be made to the present invention without departing from the spirit and scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

The invention claimed is:

1. A method for operating an acetylene hydrogenation unit of an integrated system for producing olefins, the method comprising:
  separating a first process effluent from a first olefin production process into at least a hydrogenation feed and an acetylene-depleted stream in a separation system, the hydrogenation feed comprising at least acetylene, carbon monoxide, and hydrogen;

one or both of:
  introducing at least a portion of a second process effluent from a second olefin production process to the separation system; or
  combining the at least a portion of the second process effluent with the first process effluent upstream of the separation system;
  wherein introducing the portion of the second process effluent to the separation system, combining the portion of the second process effluent with the first process effluent, or both, increases a concentration of carbon monoxide in the hydrogenation feed;
contacting the hydrogenation feed with an acetylene hydrogenation catalyst in the acetylene hydrogenation unit, the contacting causing hydrogenation of at least a portion of the acetylene in the hydrogenation feed to produce a hydrogenated effluent, wherein:
  an elevated concentration of carbon monoxide in the hydrogenation feed reduces a reaction rate of the hydrogenation of the acetylene, wherein the reduction in the reaction rate is independent of temperature;
  the elevated concentration of carbon monoxide in the hydrogenation feed is due to the portion of the second process effluent; and
  the acetylene hydrogenation unit operates at an elevated temperature relative to normal operating temperatures, wherein normal operating temperatures occur when the portion of the second effluent is not introduced to the separation system, combined with the first process effluent, or both, and wherein a concentration of acetylene in the hydrogenated effluent is less than a threshold acetylene concentration.

2. The method of claim 1, wherein the concentration of acetylene in the hydrogenated effluent does not increase above the threshold acetylene concentration during introducing the portion of the second process effluent to the separation system, combining the portion of the second process effluent with the first process effluent, or both.

3. The method of claim 1, wherein the threshold acetylene concentration is less than or equal to 2.0 ppmv, or less than or equal to 1.0 ppmv.

4. The method of claim 1, wherein:
the acetylene hydrogenation unit comprises at least a first hydrogenation reactor and a second hydrogenation reactor downstream of the first hydrogenation reactor; and
the elevated temperature of the acetylene hydrogenation unit is sufficient to increase an acetylene conversion in the first hydrogenation reactor, immediately prior to integrating the portion of the second process effluent, to greater than a threshold acetylene conversion, the threshold acetylene conversion being a minimum acetylene conversion in the first hydrogenation reactor, before integration of the portion of the second process effluent, above which the acetylene concentration in the hydrogenated effluent is maintained less than or equal to the threshold acetylene concentration after integrating the portion of the second process effluent.

5. The method of claim 4, wherein the separation system is a front end depropanizer and the threshold acetylene conversion in the first hydrogenation reactor is greater than or equal to 0.95 for a flow ratio of less than or equal to 1/12, wherein the flow ratio is a mass flow rate of a portion of the hydrogenation feed contributed by the second process effluent divided by a mass flow rate of another portion of the hydrogenation feed contributed by the first process effluent.

6. The method of claim 4, wherein:
the separation system is a front end depropanizer;
a flow ratio is from 1/12 to 1/2, the flow ratio being a mass flow rate of a portion of the hydrogenation feed contributed by the second process effluent divided by a mass flow rate of another portion of the hydrogenation feed contributed by the first process effluent; and
the threshold acetylene conversion in the first hydrogenation reactor is greater than or equal a value calculated from $\min[(-0.00024*C_{CO}+0.5*R+0.942), 0.99]$, where $C_{CO}$ is a carbon monoxide concentration in the hydrogenation feed contributed by the cracked gas in parts per million by volume of the hydrogenation feed and R is the flow ratio.

7. The method of claim 4, wherein the separation system is a front end de-ethanizer and the threshold acetylene conversion in the first hydrogenation reactor is greater than or equal to 0.99 for a flow ratio less than or equal to 1/2, wherein the flow ratio is a mass flow rate of a portion of the hydrogenation feed contributed by the second process effluent divided by a mass flow rate of another portion of the hydrogenation feed contributed by the first process effluent.

8. The method of claim 1, further comprising:
introducing a first portion of the second process effluent to the separation system, combining the first portion of the second process effluent with the first process effluent upstream of the separation system, or both, wherein introducing the first portion of the second process effluent to the separation system, combining the first portion of the second process effluent with the first process effluent, or both, increases the concentration of carbon monoxide in the hydrogenation feed and reduces the conversion of acetylene in the acetylene hydrogenation unit;
recycling a remaining portion of the second process effluent back to the second olefin production process;
increasing a temperature of the acetylene hydrogenation unit to increase the conversion of acetylene in the acetylene hydrogenation unit; and
passing at least a second portion of the second process effluent to the separation system, combining at least a second portion of the second process effluent with the first process effluent and the first portion of the second process effluent upstream of the separation system, or both, wherein integrating the at least a second portion of the second process effluent further increases the concentration of carbon monoxide in the hydrogenation feed and reduces the conversion of acetylene in the acetylene hydrogenation unit.

9. The method of claim 8, wherein a mass flow rate of a portion of the hydrocarbon feed contributed by the first portion of the second process effluent is greater than 0% and less than or equal to 12% of the mass flow rate of another portion of the hydrogenation feed contributed by the first process effluent.

10. The method of claim 1, further comprising increasing a carbon monoxide concentration of the first process effluent prior to introducing the at least a portion of the second process effluent.

11. The method of claim 10, further comprising, after introducing the portion of the second process effluent, decreasing a concentration of carbon monoxide in the first process effluent.

12. The method of claim 4, wherein the acetylene hydrogenation unit comprises at least a third hydrogenation reactor downstream of the second hydrogenation reactor.

13. The method of claim 1, wherein the hydrogenation feed comprises at least one product, the at least one product comprising one or more of ethylene, propylene, methane, ethane, propane, or combinations of these.

14. The method of claim 1, wherein the first process effluent is a cracked gas from a steam cracking system, and the second process effluent is a fluidized catalytic cracking effluent from a fluidized catalytic cracking (FCDh) system.

15. A method for operating an acetylene hydrogenation unit of a steam cracking system that integrates a fluidized catalytic dehydrogenation (FCDh) effluent from a fluidized catalytic dehydrogenation (FCDh) system, the method comprising:

cracking at least a portion of a first hydrocarbon feed in a steam cracking unit to produce a cracked gas;

separating the cracked gas into at least a hydrogenation feed and acetylene-depleted stream in a separation system, the hydrogenation feed comprising at least acetylene, carbon monoxide, hydrogen, and at least one product;

contacting the hydrogenation feed with an acetylene hydrogenation catalyst in the acetylene hydrogenation unit comprising at least a first hydrogenation reactor and a second hydrogenation reactor, the contacting causing hydrogenation of at least a portion of the acetylene in the hydrogenation feed to produce a hydrogenated effluent;

increasing a temperature of the hydrogenation feed such that a conversion of acetylene in the first hydrogenation reactor is greater than or equal to a threshold acetylene conversion, the threshold acetylene conversion being a minimum acetylene conversion in the first hydrogenation reactor, before integration of the portion of the FCDh effluent, above which the acetylene concentration in the hydrogenated effluent is maintained less than or equal to the threshold acetylene concentration after integrating the portion of the FCDh effluent; and dehydrogenating at least a portion of a second hydrocarbon feed in the FCDh system to produce the FCDh effluent, the FCDh effluent having a concentration of carbon monoxide greater than a concentration of carbon monoxide in the cracked gas;

introducing at least a portion of the FCDh effluent to the separation system, combining at least a portion of the FCDh effluent with the cracked gas upstream of the separation system, or both, wherein introducing the portion of the FCDh effluent to the separation system, combining the portion of the FCDh effluent with the cracked gas, or both, increases a concentration of carbon monoxide in the hydrogenation feed, wherein an elevated concentration of carbon monoxide in the hydrogenation feed due to the portion of the FCDh effluent reduces a reaction rate of the hydrogenation of the acetylene, wherein the reduction in the reaction rate is independent of temperature; and the elevated temperature of the acetylene hydrogenation unit relative to normal operating temperatures maintains the concentration of acetylene in the hydrogenated effluent less than or equal to a threshold acetylene concentration, wherein normal operating temperatures occur when the portion of the FCDh effluent is not introduced to the separation system, combined with the cracked gas, or both.

* * * * *